United States Patent
Kirkpatrick et al.

(10) Patent No.: US 10,745,757 B2
(45) Date of Patent: Aug. 18, 2020

(54) COMPOSITIONS AND METHODS FOR DETERMINING LIKELIHOOD OF AN INCREASED SUSCEPTIBILITY TO CONTRACTING JOHNE'S DISEASE

(71) Applicant: Wisconsin Alumni Research Foundation, Madison, WI (US)

(72) Inventors: Brian W. Kirkpatrick, Fitchburg, WI (US); George E. Shook, Middleton, WA (US); Michael T. Collins, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/371,420

(22) Filed: Apr. 1, 2019

(65) Prior Publication Data

US 2019/0226028 A1    Jul. 25, 2019

Related U.S. Application Data

(63) Continuation of application No. 12/861,482, filed on Aug. 23, 2010, now Pat. No. 10,294,528.

(51) Int. Cl.
| | |
|---|---|
| *C12Q 1/68* | (2018.01) |
| *C12P 19/34* | (2006.01) |
| *C12Q 1/6883* | (2018.01) |

(52) U.S. Cl.
CPC ...... *C12Q 1/6883* (2013.01); *C12Q 2600/118* (2013.01); *C12Q 2600/124* (2013.01); *C12Q 2600/156* (2013.01)

(58) Field of Classification Search
CPC ...... C12Q 1/6827; C12Q 1/68; C12Q 1/6816; C12P 19/34
See application file for complete search history.

(56) References Cited

PUBLICATIONS

Settles M. et al. "A whole genome association analysis identifies loci associated with *Mycobacterium avium* subsp. paratuberculosis infection status in US holstein cattle" Anim Genet. Oct. 2009;40(5):655-62. Electronic publication Apr. 24, 2009. (Year: 2009).*
Luan, Tu, J. Woolliams, and T. Meuwissen. "The contribution of linkage and linkage disequilibrium information to the accuracy of genomic selection." 9th World Congress on Genetics Applied to Livestock Production. vol. 1318. 2006. (Year: 2006).*

* cited by examiner

*Primary Examiner* — Stephen T Kapushoc
(74) *Attorney, Agent, or Firm* — Boyle Fredrickson S.C.

(57) ABSTRACT

Collections of polynucleotides useful for estimating breeding value or detecting likelihood of an increased susceptibility to contracting paratuberculosis are disclosed. The polynucleotides are used to detect genomic sequences quantitatively associated with an increased susceptibility to contracting paratuberculosis. Methods for using the collections to estimate breeding value or predict likelihood of an increased susceptibility to contracting paratuberculosis are also provided. Kits comprising the collection of polynucleotides are also provided.

9 Claims, 3 Drawing Sheets

Specification includes a Sequence Listing.

COMPOSITIONS AND METHODS FOR DETERMINING LIKELIHOOD OF AN INCREASED SUSCEPTIBILITY TO CONTRACTING JOHNE'S DISEASE

CROSS-REFERENCE TO RELATED APPLICATIONS

This application is a continuation of U.S. patent application Ser. No. 12/861,482, filed Aug. 23, 2010, which is incorporated by reference herein.

STATEMENT REGARDING FEDERALLY SPONSORED RESEARCH

This invention was made with government support under 2007-35205-17884, 00-52100-9621 and 01-CRHF-0-6055 awarded by the USDA/CSREES. The government has certain rights in the invention.

FIELD OF THE INVENTION

This related generally to animal genetics and improvements in cattle breeding. More particularly, it relates to compositions and methods for predicting an increased susceptibility to contracting paratuberculosis in cattle.

BACKGROUND

Paratuberculosis, commonly called Johne's disease, is a chronic infection of the small intestine caused by *Mycobacterium avium*, ssp. *paratuberculosis* ("MAP"). Paratuberculosis occurs in a wide variety of animals, but most often in ruminants, especially cattle. The disease presents with symptoms including diarrhea, severe weight loss and decres=ased milk production. Cattle normally become infected with MAP as calves, but because of the slowly progressive nature of the infection, clinical signs of paratuberculosis are usually not seen until animals are adults. There is no cure for the disease and infected animals ultimately become emaciated and must be removed from the herd much sooner than their non-infected counterparts.

Since the signs of paratuberculosis can be confused with the signs of several other diseases, a diagnosis can be confirmed only by use of laboratory tests. The best way to avoid paratuberculosis is to be as certain as possible that animals brought into the herd are not infected with MAP. There are currently three common ways to test animals for paratuberculosis: culture of fecal samples, DNA probe on fecal samples, and blood tests for antibodies to MAP. The fecal culture tests take 8 to 16 weeks because of the extremely slow growth rate of MAP. MAP bacteria can also be detected in fecal samples by use of sophisticated DNA probe tests. DNA probes are much faster than culturing the organism and can be done within three days. Unfortunately, the commercial kit for doing the DNA probe tests are not yet as sensitive as culture and are only able to detect infected animals when their infection has progressed to the stage where large numbers of MAP are being excreted in the feces. Therefore, animals in early stages of the infection are not detected. There are several blood tests for paratuberculosis, but ELISA tests are considered the most accurate and best standardized. Three ELISA-based tests are licensed by the U.S. Department of Agriculture for detection of MAP-infected cattle. The ELISA tests are fast, simple, inexpensive and able to detect animals that are infected before they show signs of paratuberculosis.

However, all of these test results come too late. The animal is already infected. In addition, tests performed on individual animals are not 100% sensitive, meaning they cannot detect 100% of all infected animals. Instead, the tests are performed on a group of animals to extrapolate that if an entire group tests negative, then the probability the group is free of MAP infection is very high.

Methods for paratuberculosis control depend on the type of animal and the patterns of husbandry. In principle, two strategies must be employed at the same time:
1. newborn animals must be protected from infection by being born and raised in a clean environment and fed milk free of MAP; and
2. adult animals carrying the MAP infection must be identified by laboratory tests and removed from the herd, flock or enclosure.

A national study of US dairies, Dairy NAHMS 96, found that approximately 22% of US dairy farms have at least 10% of the herd infected with paratuberculosis. The study determined that infected herds experience an average loss of $40 per cow in herds with a low paratuberculosis clinical cull rate, while herds with a high paratuberculosis clinical cull rate lost on average of $227 per cow. This loss was due to reduced milk production, early culling, and poor conditioning at culling. The cost of paratuberculosis in beef herds still needs to be determined.

Therefore, there remains a need for methods of predicting animals that have an increased susceptibility of contracting paratuberculosis and selectively breed away from that increased susceptibility. Paratuberculosis is a good candidate for genetic selection because a) an effective vaccine is not available, b) the disease is not curable, c) it causes significant economic losses, and d) it is potentially zoonotic. Selective breeding to reduce disease susceptibility would be a low cost, sustainable practice.

Previous reports of association of DNA markers with paratuberculosis susceptibility have been limited, and frequently focused on candidate genes. The nucleotide-binding oligomerization domain containing 2 gene (NOD2), previously referred to as the caspase recruitment domain 15 protein gene (CARD15), is a well characterized gene that contributes to predisposition to Crohn's disease in humans (see recent reviews by Hugot (2006) and Radford-Smith and Pandeya (2006)) and has been the subject of study in cattle as a candidate gene. Taylor et al. (2006) identified 36 NOD2 polymorphisms in a screening of 42 animals from ten different breeds. Association of these polymorphisms with infection could not be adequately tested owing to a paucity of infected animals (n=11). Subsequently, Pinedo et al. (2009a) tested association of three of the NOD2 polymorphisms identified by Taylor et al. (2006) in a case-control study using cattle of dairy (Holstein, Jersey) and beef (Brahman×Angus) types. An association significant at a nominal P<0.01, after controlling for breed, was found for a non-synonymous SNP in the leucine-rich repeat domain of the gene. Evidence for this association came principally from the Brahman×Angus subset of the data. The same data was subsequently re-analyzed considering effects of predicted SNP haplotypes. A haplotype based on two non-synonymous NOD2 SNPs was found significantly associated with infection status (nominal P<0.0001) in an analysis that did not account for breed. The effect attributable to this risk haplotype was due to greater incidence of infection in animals heterozygous for the haplotype (i.e. overdominance). This is in contrast to the effects associated with NOD2 alleles associated with susceptibility to Crohn's disease in humans where the affects manifest in a partial recessive fashion with genotype relative risk increasing exponentially between risk allele heterozygotes to homozygotes or compound heterozygotes (Economou et al. 2004). Analysis of the NOD2 locus in US Holstein cattle in the author's laboratory (unpublished) revealed additional polymorphisms, but none of nine previously or newly identified SNPs genotyped were significantly associated with infection status in a case-control study using 169 case (positive to either ELISA or fecal culture tests or both) and 188 control cows. In addition, only weak evidence of SNP association with infection status was observed for bovine chromosome 18 (location of NOD2) in whole-genome association analyses reported herein. Pinedo et al. (2009a) point out that the NOD2 allele showing association is more frequent in the Brahman×Angus cattle than in the Holstein cattle they utilized which could account for the lack of association observed in the current work with Holsteins.

Only two whole genome scans for paratuberculosis susceptibility have been previously reported. Our earlier study of three large sire families (264 to 585 daughters per sire) from Population 1 examined 159 informative microsatellite markers across all 29 autosomal chromosomes. One significant (chromosome-wide P-value=0.032) region on chromosome 20 was found, but the wide spacing of the markers made it impossible to more narrowly localize the region (Gonda et al., 2007). Power of this study was lessened by low marker density and the consideration only of linkage effects. The other previously reported whole genome scan utilized the recently available bovine 50 k SNP set to greatly improve marker density. Settles et al. (2009) used 218 Holstein cows in a case-control design to assess marker association with MAP infection under various definitions of infected phenotype. Phenotypes were assigned based on culture of MAP from fecal and tissue samples (ileum, ileo-cecal valve and ileo-cecal lymph nodes). 112 animals were negative to both tests, with the remainder positive to one or both fecal or tissue culture. Composition of case and control groups varied depending on definition of phenotype (fecal-positive vs. fecal-negative, tissue-positive vs. tissue-negative, etc.) leading in some instances to a small number of case samples (range 25-90). Suggestive associations ($p<5\times10^{-5}$) were found under various phenotypic definitions on chromosomes 1, 3, 5, 7, 8, 9, 16, 21 and 23. Correspondence between the results reported here and results reported by Settles et al. (2009) are slight, and none are the specific SNPs that Settles et al. found most significant.

Crohn's disease in humans bears some similarity to Johne's disease in cattle in its manifestation, and as a consequence, genes implicated in the development of Crohn's disease have been considered as candidate genes in the study of Johne's disease. Whole genome association (WGA) studies of Crohn's disease in humans (Barrett et al. 2008; Raelson et al. 2007; Welcome Trust Case Control Consortium 2007; Parkes et al. 2007; Rioux et al. 2007; Libioulle et al. 2007) have been more numerous and of larger scale than the study reported herein. Validated results from human Crohn's disease WGA studies, compilation viewable at www.genome.gov/26525384 (Hindorff et al. 2009), have now implicated more than 30 unique chromosomal regions in humans. The correspondence between results reported here or by Settles et al. (2009) for cattle and the results from humans is limited. Applying an arbitrary and liberal constraint of significant human and bovine markers being within a distance of 4 Mb, only the associations reported by Settles et al. (2009) on proximal BTA9 show correspondence with human WGA results and only associations on BTA7 and 20 reported herein show correspondence. Prostaglandin E receptor 4 (PTGER4) and the immunity-related GTPase family, M gene (IRGM), have been identified as candidate genes for the regions corresponding to BTA7 and 20, respectively in human studies. Regarding PTGER4, Libioulle et al. (2007) identified and validated SNP associations in a 1.25 Mb gene desert on HSA5 adjacent to PTGER4 and found SNP associations with variation in PTGER4 expression. Prior work has found that PTGER4 knock-out mice develop severe colitis upon treatment with dextran sodium sulphate, unlike knock-outs for other prostaglandin receptors (Kabashima et al. 2002) supporting its consideration as a candidate gene. Regarding IRGM, The most significant SNP on BTA7 is located within 2 Mb of the location of IRGM, a candidate gene for Crohn's disease in humans based on results from three whole genome association studies (Barrett et al. 2008, Welcome Trust Case Control Consortium 2007, Parkes et al. 2007) and subsequent studies. The SNPs significantly associated with Crohn's disease in this case flanked the IRGM gene, and subsequent analyses failed to reveal non-synonymous SNPs with the IRGM coding regions leading to speculation that functional polymorphism might alter regulation of IRGM. Subsequent work by McCarroll et al. (2008) identified a 20 kb insertion—deletion polymorphism upstream of IRGM that correlated with differences in IRGM expression, and the authors have speculated that this difference in IRGM expression may related to differences in autophagy.

SUMMARY OF THE INVENTION

This disclosure relates generally to identification and the use of a collection of polynucleotide sequences, or polynucleotides, for detecting (by any means known in the art) an at least partially complementary sequence in a cow genome relating to paratuberculosis.

The presence or absence of the at least partially complementary sequences, i.e. the sequences in the cow genome, is quantitatively associated with the trait of an increased susceptibility to contracting paratuberculosis in a cattle population. In various embodiments, the collection comprises at least one sequence that is quantitatively associated with an increased susceptibility to contracting paratuberculosis with statistical significance of at least $p\leq0.01$. Preferred are those collections comprising at least one sequence that is quantitatively associated with an increased susceptibility to contracting paratuberculosis with statistical significance of at least $p\leq0.001$, or even less.

Also provided herein are methods of using the collections for predicting or estimating the likelihood of an increased susceptibility to contracting paratuberculosis. The methods generally comprise the steps of:
  a) providing a collection of one or more polynucleotides, each of which is at least partially complementary to a sequence in a cow genome, comprising at least one sequence that is quantitatively associated with an increased susceptibility to contracting paratuberculosis with statistical significance of at least $p\leq0.01$;
  b) using the collection to determine the presence or absence of sequences complementary to one or more polynucleotides from the collection in one or more members of the cattle population genome, wherein the presence or absence of the complementary sequences is quantitatively associated with the trait of an increased susceptibility to contracting paratuberculosis in a cattle population; and c) estimating the likelihood of an increased susceptibility to contracting paratuberculosis based on the results of step b).

Kits providing the collections and instructions for using them in predicting the likelihood of an increased susceptibility to contracting paratuberculosis are also provided.

Other and further objects, features, and advantages of the present invention will be readily apparent to those skilled in the art.

DETAILED DESCRIPTION

Figure 1:
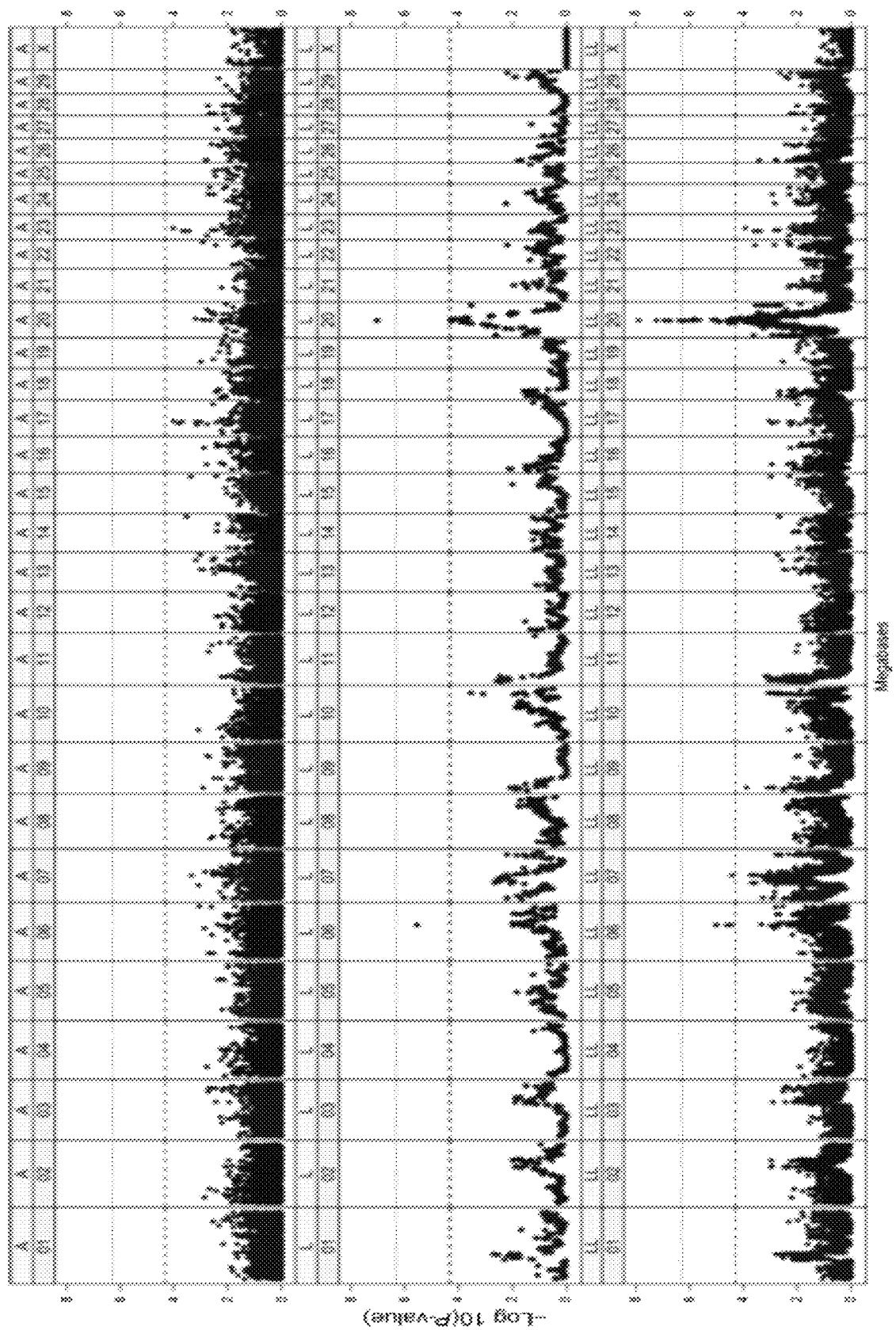
FIG. 1: Results of whole genome scan of Population 1 for genetic marker association with susceptibility to infection of cattle by MAP. Vertical panels denote individual chromosomes as indicated at the top of each panel. Each point represents the –log 10 of the P-value (y-axis) from linkage disequilibrium (top; "A"), linkage (center; "L") and combined linkage-linkage disequilibrium (bottom; "LL") analyses, relative to genomic location of the SNP marker (x-axis). A total of 35,772 polymorphic SNP markers were included in the analysis. The dashed and dotted lines represent p-values of $5\times10^{-5}$ and $1\times10^{-7}$, respectively, corresponding to suggestive and significant results.

The present application incorporates by reference SEQ ID NO: 1-197 provided herewith on a the files titled All_SNP_081810.txt and Preferred_SNP_081810.txt, created on Aug. 18, 2010.

Definitions the following abbreviations may be used herein:
cM, centiMorgan;
CWER, comparison-wise error rates;
FDS, false discovery rate;
HWE, Hardy-Weinberg equilibrium;
IBD, identity by descent;
Kb, kilobase;
LD, linkage disequilibrium;
LLD, linkage-linkage disequilibrium;
LRT, log-likelihood ratio;

MAF, minor allele frequency;
MB, megabase;
NCBI, National Center for Biotechnology Information;
PEV, prediction error variance;
PTA, predicted transmitting ability;
QTL, quantitative trail loci;
SNP; single nucleotide polymorphism;

The term "individual" when referring to an animal means an individual animal of any species or kind.

The term "animal" is used in a general sense and means a human or other animal, including avian, bovine, canine, equine, feline, hicrine, lupine, murine, ovine, and porcine animals. Preferably the animal is a mammal, particularly a bovine. Unless otherwise specified, or clear from the context, the term "mammal" herein includes human.

As used herein, "linkage disequilibrium" (or "LD") refers to allelic association between specific alleles at two or more neighboring loci in the genome, e.g., within a population. LD can be determined for a single marker or locus, or multiple markers. LD is sometimes expressed herein as $r^2$ values where $r^2=1/(4N_e c+1)$ where c=recombination rate (M), and Ne=effective population size. (Sved, 1971)

As used herein, "allele" refers to one or more alternative forms of a particular sequence that contains an SNP. The sequence may or may not be within a gene, and may be within a coding or noncoding portion and such a gene, and may be within an exon or an intron of a particular gene.

"Quantitative trait locus," (or "QTL"), as used herein is a genomic sequence that is associated with a particular phenotypic trait. Multiple QTL may be identified for a particular trait, and they are frequently found on different chromosomes. The number of QTLs that associate significantly with a particular phenotypic trait may provide an indication of the genetic architecture of a trait, the number of genes that affect the trait, or the extent of the affect of one or more of those genes. One or more QTL that significantly associates with a trait may be candidate genes underlying that trait, which can be sequenced and identified. The significance of the degree of association of a given QTL with a particular trait can be assessed statistically, e.g. through QTL mapping of the alleles that occur in a locus and the phenotypes that they produce. Statistical analysis is preferred to demonstrate whether an observed association with a trait is significant. The presence of a QTL, and its location identify a particular region of the genome as potentially containing a gene that is associated, directly (e.g., structurally) or indirectly (e.g., regulatory) with the trait being analyzed. The probability of association can be plotted for various markers associated with the trait spaced across a chromosome, or throughout the genome.

A "polynucleotide" includes single-stranded or a multi-stranded nucleic acid molecules comprising two or more sequential bases, including any single strand or parallel and anti-parallel strands of a multi-stranded nucleic acid. Polynucleotide may be of any length, and thus, include very large nucleic acids, as well as short ones, such as oligonucleotides.

The term "oligonucleotide" typically refers to short polynucleotides, generally no greater than about 50 nucleotides. It will be understood that if a nucleotide sequence is denoted represented by a DNA sequence (i.e., A, T, G, C), the corresponding RNA sequence (i.e., A, U, G, C, wherein "U" replaces "T") is also included.

As used throughout, ranges herein are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values or 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, and so on.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a SNP", "a method", or "a trait" includes a plurality of such "SNPs", "methods", or "traits." Reference herein, for example to "an association" includes a plurality of such associations, whereas reference to "chromosomes" includes a single chromosome where such' interpretation is not precluded from the context. Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Where used herein the term "examples," particularly when followed by a listing of terms is merely exemplary and illustrative, and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not cited fully within the specification are set forth at the end of the specification.

Details

In a first of its several aspects, this disclosure relates to a collection of polynucleotide sequences, or polynucleotides, each of which is at least partially complementary to a sequence in a cow genome. The presence or absence of the at least partially complementary sequences, i.e. the sequences in the cow genome, is quantitatively associated with the trait of an increased susceptibility to contracting paratuberculosis in a cattle population. In various embodiments, the collection comprises at least one sequence that is quantitatively associated with an increased susceptibility to contracting paratuberculosis with statistical significance of at least $p \leq 0.01$. Preferred are those collections comprising at least one sequence that is quantitatively associated with an increased susceptibility to contracting paratuberculosis with statistical significance of at least $p \leq 0.001$, or even less. In various embodiments, the statistical significance of the quantitative association with an increased susceptibility to contracting paratuberculosis is $p \leq 0.001$, $p \leq 0.0009$, $p \leq 0.0008$, $p \leq 0.0007$, $p \leq 0.0006$, $p \leq 0.0005$, or even less. Most preferred are embodiments that have statistical significance of $p \leq 10\text{-}4$, 10-5, or even 10-6, or lower. Thus, the more highly significant (i.e., the lower the p value) the association is, the more useful the polynucleotide collection can be for predicting an increased susceptibility to contracting paratuberculosis. In certain embodiments, polynucleotides useful for indicating the presence or absence of genomic sequences whose association with an increased susceptibility to contracting paratuberculosis is, from a statistical view, only suggestive, may be useful herein. More preferred are those polynucleotides useful for indicating the presence or absence of genomic sequences whose association with an increased susceptibility to contracting paratuberculosis is highly suggestive, significant, or even highly significant. The skilled artisan will understand that the statistical significance levels deemed suggestive, highly suggestive, significant, or highly significant will vary based on the particular statistical measures used, and the underlying data used to generate the measures of association. Examples of such statistical measures are shown in the working examples.

The collection of polynucleotides is useful for predicting an increased susceptibility to contracting paratuberculosis rate or likelihood of an increased susceptibility to contracting paratuberculosis within an individual member of a population, or within a herd, and is also useful for other purposes, such as estimating breeding value in cattle, whether for genetic purposes (e.g. breed improvement, herd management, and the like), or for economic considerations (e.g., determining or estimating sale or replacement value of an animal or reproductive material from an animal, predicting the value of offspring, estimating gain or loss for milk or meat production (e.g., practical cost or impact of an increased susceptibility to contracting paratuberculosis for farmer) or the like), or a combination thereof.

The polynucleotides in the collection can be any sequences, for example, they could encompass a portion of structural genes, regulatory genes, or other sequences, e.g., SNPs, microsatellite sequences, or other sequences of any length found in a genome. The polynucleotides of the collections may correspond to either strand of a nucleic acid heteroduplex. In some embodiments, the polynucleotides are completely complementary to a portion of a genome, while in others they may be less than completely complementary, provided that they are useful for detecting at least a partially complementary sequence in the genome. For example, in various applications the polynucleotides may be used as primers for amplifying specific sequences to be detected, which may not require 100% complementarity. In other embodiments, the polynucleotide may be used as probes for binding to various sequences to be detected. In one presently preferred embodiment, each polynucleotide is useful for detecting the presence or absence of one allele of an SNP in the cow genome. In other embodiments, each polynucleotide comprises one allele of an SNP in the cow genome, or its complement.

The collection can comprise sequences distributed throughout the genome. In one embodiment of the collection, at least one of the polynucleotides is complementary to a sequence located on any bovine chromosome. In one embodiment, the preferred chromosomes include one or more of chromosomes 2, 3, 4, 5, 6, 7, 9, 10, 13, 14, 15, 16, 17, 18, 20, 21, 22, 23, 25, 26 and 29.

In another, bovine chromosome 13 (BTA13) is preferred. Especially preferred are particular regions of chromosome 13, including those that are near or encode certain genes. In another embodiment, at least one of the polynucleotides is complementary to a sequence that maps between 4-71 Mb of BTA7. In various embodiments, the collection comprises one or more polynucleotides complementary to a sequence that maps at either of 4-6 Mb, 31-34 Mb or 70-72 Mb of BTA7.

In another, bovine chromosome 16 (BTA16) is preferred. Especially preferred are particular regions of chromosome 16, including those that are near or encode certain genes. In another embodiment, at least one of the polynucleotides is complementary to a sequence that maps between 21-70 Mb of BTA16. In various embodiments, the collection comprises one or more polynucleotides complementary to a sequence that maps at either of 21-23 Mb or 60-70 Mb of BTA7.

In another, bovine chromosome 20 (BTA20) is preferred. In one embodiment, at least one of the polynucleotides is complementary to a sequence that maps between 31-67 Mb of BTA20. Especially preferred are particular regions of chromosome 20, including those that are near or encode certain genes. In various embodiments, the collection comprises one or more polynucleotides complementary to a sequence that maps on BTA20 at either of 31-35 Mb or 65-68 Mb of BTA20. In a currently preferred embodiment, at least one of the polynucleotides is complementary to a sequence that maps between 31-35 Mb of BTA20.

In another, bovine chromosome 21 (BTA21) is preferred. Especially preferred are particular regions of chromosome 21, including those that are near or encode certain genes. In another embodiment, at least one of the polynucleotides is complementary to a sequence that maps between 19-68 Mb of BTA7. In various embodiments, the collection comprises one or more polynucleotides complementary to a sequence that maps at either of 19-25 Mb or 61-69 Mb of BTA7.

In another, bovine chromosome 26 (BTA26) is preferred. In one embodiment, at least one of the polynucleotides is complementary to a sequence that maps between 34-40 Mb of BTA26. Also useful are polynucleotides that can identify the presence or absence of sequences which map to various overlapping or more specific locations, as set forth in the Examples below.

In one presently preferred embodiment, the collection comprise at least one polynucleotide complementary to a sequence located with high LD to a genomic sequence for Prostaglandin E receptor 4 ("PTGER4"). In another presently preferred embodiment, the collection comprises at least one polynucleotide complementary to a sequence located with high LD to a genomic sequence for immunity-related GTPase family, M gene ("IRGM"). Certain preferred collections of polynucleotides feature one or more sequences that can be used to identify the presence or absence of, for example, SNPs within PTGER4 or IRGM. PTGER4 and IRGM each has been identified herein as a positional candidate that is significantly associated with an increased susceptibility to contracting Crohn's disease. However, of the more than 30 unique human chromosomal regions implicated by previous studies, correspondence between results between cattle and human is limited.

The collection can also comprise at least one polynucleotide useful for detecting one or more specific SNPs. For example, the SNPs given in Table A have been quantitatively associated with an increased susceptibility to contracting paratuberculosis, and are thus sequences for detecting their presence are useful herein.

In various embodiments of the collections or the methods below, the SNPs comprise one or more of the SNPs listed in Table A.

TABLE A

SNPs Useful for Predicting An Increased Susceptibility To Contracting Paratuberculosis

|  | SNP_ID | BTA/Mb | Chi-squared | P-value |
|---|---|---|---|---|
| SEQ ID NO 1 | Hapmap57166-rs29020401 | 13/34.10 | 38.57 | 4.21E-09 |
| SEQ ID NO 2 | ARS-BFGL-NGS-63936 | 20/36.42 | 30.03 | 3.01E-07 |
| SEQ ID NO 3 | ARS-BFGL-NGS-84088 | 20/35.59 | 29.61 | 3.71E-07 |
| SEQ ID NO 4 | ARS-BFGL-BAC-13827 | 13/33.53 | 29.51 | 3.9E-07 |
| SEQ ID NO 5 | Hapmap52062-rs29027270 | 26/43.49 | 28.74 | 5.75E-07 |
| SEQ ID NO 6 | ARS-BFGL-NGS-95663 | 20/33.46 | 28.5 | 6.48E-07 |
| SEQ ID NO 7 | Hapmap48854-BTA-69129 | 3/103.69 | 28.34 | 7.02E-07 |
| SEQ ID NO 8 | Hapmap51130-BTA-105627 | 23/32.11 | 27.96 | 8.47E-07 |
| SEQ ID NO 9 | ARS-BFGL-NGS-38328 | 13/33.67 | 27.65 | 9.93E-07 |
| SEQ ID NO 10 | ARS-BFGL-NGS-38574 | 20/38.27 | 27.55 | 1.04E-06 |
| SEQ ID NO 11 | ARS-BFGL-NGS-23255 | 26/34.93 | 27.24 | 1.22E-06 |
| SEQ ID NO 12 | BTA-13956-no-rs | 14/64.31 | 26.75 | 1.55E-06 |
| SEQ ID NO 13 | Hapmap54042-ss46526396 | 22/12.41 | 26.22 | 2.02E-06 |
| SEQ ID NO 14 | BTB-00261837 | 6/66.68 | 25.88 | 2.4E-06 |
| SEQ ID NO 15 | ARS-BFGL-NGS-16165 | 16/64.91 | 25.53 | 2.86E-06 |
| SEQ ID NO 16 | ARS-BFGL-NGS-114768 | 26/38.92 | 25.11 | 3.52E-06 |
| SEQ ID NO 17 | ARS-BFGL-NGS-84831 | 21/21.94 | 24.82 | 4.07E-06 |
| SEQ ID NO 18 | ARS-BFGL-NGS-55787 | 12/36.31 | 24.8 | 4.11E-06 |
| SEQ ID NO 19 | ARS-BFGL-NGS-18067 | 22/12.45 | 24.72 | 4.28E-06 |
| SEQ ID NO 20 | ARS-BFGL-NGS-114979 | 23/16.63 | 24.71 | 4.31E-06 |
| SEQ ID NO 21 | Hapmap41410-BTA-104176 | 7/63.04 | 24.67 | 4.4E-06 |
| SEQ ID NO 22 | ARS-BFGL-NGS-84327 | 13/5.54 | 24.39 | 5.05E-06 |
| SEQ ID NO 23 | ARS-BFGL-NGS-116261 | 19/61.05 | 24.27 | 5.36E-06 |
| SEQ ID NO 24 | BTB-00779241 | 20/35.78 | 24.19 | 5.6E-06 |
| SEQ ID NO 25 | Hapmap51169-BTA-122103 | 7/56.17 | 24.11 | 5.82E-06 |
| SEQ ID NO 26 | ARS-BFGL-BAC-31757 | 20/67.43 | 23.8 | 6.79E-06 |
| SEQ ID NO 27 | Hapmap51780-BTA-93959 | 18/38.44 | 23.62 | 7.41E-06 |
| SEQ ID NO 28 | BTB-00553468 | 14/18.76 | 23.47 | 0.000008 |

TABLE A-continued

SNPs Useful for Predicting An Increased Susceptibility
To Contracting Paratuberculosis

| | SNP_ID | BTA/Mb | Chi-squared | P-value |
|---|---|---|---|---|
| SEQ ID NO 29 | Hapmap42075-BTA-114094 | 16/69.88 | 23.28 | 8.79E−06 |
| SEQ ID NO 30 | BTB-01278461 | 4/85.43 | 23.14 | 9.43E−06 |
| SEQ ID NO 31 | ARS-BFGL-NGS-12828 | 26/37.06 | 23.1 | 9.63E−06 |
| SEQ ID NO 32 | BTA-116871-no-rs | 17/28.19 | 23.07 | 9.77E−06 |
| SEQ ID NO 33 | Hapmap46604-BTA-35152 | 14/60.13 | 23.06 | 9.82E−06 |
| SEQ ID NO 34 | BTA-15204-no-rs | 20/34.74 | 23.05 | 9.86E−06 |
| SEQ ID NO 35 | BTA-61435-no-rs | 26/36.89 | 22.96 | 1.04E−05 |
| SEQ ID NO 36 | Hapmap51346-BTA-89239 | 9/6.17 | 22.92 | 1.05E−05 |
| SEQ ID NO 37 | Hapmap49609-BTA-43790 | 18/51.49 | 22.88 | 1.07E−05 |
| SEQ ID NO 38 | Hapmap38462-BTA-110556 | 20/58.48 | 22.81 | 1.11E−05 |
| SEQ ID NO 39 | Hapmap30871-BTA-158348 | 8/64.55 | 22.72 | 1.16E−05 |
| SEQ ID NO 40 | ARS-BFGL-NGS-106176 | 23/23.10 | 22.58 | 1.25E−05 |
| SEQ ID NO 41 | ARS-BFGL-NGS-31976 | 13/71.05 | 22.19 | 1.52E−05 |
| SEQ ID NO 42 | BTA-21660-no-rs | 12/35.67 | 22.16 | 1.54E−05 |
| SEQ ID NO 43 | BTB-00170785 | 4/25.67 | 22.08 | 0.000016 |
| SEQ ID NO 44 | ARS-BFGL-NGS-10383 | 10/47.26 | 22.01 | 1.66E−05 |
| SEQ ID NO 45 | Hapmap56950-ss46526304 | 3/114.08 | 21.99 | 1.68E−05 |
| SEQ ID NO 46 | ARS-BFGL-NGS-14399 | 12/36.16 | 21.62 | 2.02E−05 |
| SEQ ID NO 47 | ARS-BFGL-NGS-114316 | 26/38.21 | 21.6 | 2.04E−05 |
| SEQ ID NO 48 | BTB-01219956 | 26/12.53 | 21.57 | 2.07E−05 |
| SEQ ID NO 49 | Hapmap24928-BTC-010710 | 14/28.42 | 21.52 | 2.12E−05 |
| SEQ ID NO 50 | ARS-BFGL-NGS-34049 | 20/35.27 | 21.38 | 2.28E−05 |
| SEQ ID NO 51 | ARS-BFGL-NGS-116806 | 20/36.51 | 21.2 | 2.49E−05 |
| SEQ ID NO 52 | ARS-BFGL-NGS-13451 | 16/70.81 | 21.18 | 2.52E−05 |
| SEQ ID NO 53 | UA-IFASA-8974 | 20/31.97 | 21.14 | 2.57E−05 |
| SEQ ID NO 54 | Hapmap27079-BTC-039967 | 6/51.32 | 21.11 | 2.61E−05 |
| SEQ ID NO 55 | ARS-BFGL-NGS-84112 | 4/102.05 | 20.77 | 3.08E−05 |
| SEQ ID NO 56 | ARS-BFGL-BAC-32359 | 20/47.27 | 20.73 | 3.15E−05 |
| SEQ ID NO 57 | ARS-BFGL-NGS-101744 | 15/69.30 | 20.63 | 3.31E−05 |
| SEQ ID NO 58 | Hapmap41219-BTA-29565 | 24/32.30 | 20.53 | 3.48E−05 |
| SEQ ID NO 59 | Hapmap50053-BTA-61516 | 26/38.98 | 20.49 | 3.55E−05 |
| SEQ ID NO 60 | ARS-BFGL-NGS-115504 | 25/21.17 | 20.45 | 3.62E−05 |
| SEQ ID NO 61 | BTB-00780124 | 20/35.88 | 20.22 | 4.07E−05 |
| SEQ ID NO 62 | ARS-BFGL-NGS-101940 | 21/19.58 | 20.16 | 4.19E−05 |
| SEQ ID NO 63 | ARS-BFGL-BAC-34694 | 16/58.70 | 20.14 | 4.23E−05 |
| SEQ ID NO 64 | Hapmap59495-rs29020511 | 24/32.95 | 20.03 | 4.47E−05 |
| SEQ ID NO 65 | ARS-BFGL-NGS-3711 | 13/48.43 | 19.82 | 4.96E−05 |
| SEQ ID NO 66 | BTB-01342789 | 1/18.87 | 19.76 | 5.12E−05 |
| SEQ ID NO 67 | ARS-BFGL-NGS-91446 | 3/109.35 | 19.73 | 5.19E−05 |
| SEQ ID NO 68 | Hapmap50774-BTA-76325 | 6/51.29 | 19.7 | 5.26E−05 |
| SEQ ID NO 69 | ARS-BFGL-NGS-32123 | 15/43.28 | 19.7 | 5.26E−05 |
| SEQ ID NO 70 | BTB-01843749 | 9/35.20 | 19.57 | 5.63E−05 |
| SEQ ID NO 71 | ARS-BFGL-NGS-29032 | 16/61.38 | 19.45 | 5.98E−05 |
| SEQ ID NO 72 | Hapmap49679-BTA-61690 | 26/42.56 | 19.38 | 6.18E−05 |
| SEQ ID NO 73 | BTA-90616-no-rs | 20/29.25 | 19.32 | 6.37E−05 |
| SEQ ID NO 74 | BTA-100341-no-rs | 26/34.88 | 19.31 | 6.42E−05 |
| SEQ ID NO 75 | ARS-BFGL-NGS-30004 | 23/16.66 | 19.29 | 6.48E−05 |
| SEQ ID NO 76 | ARS-BFGL-NGS-41833 | 20/66.58 | 19.21 | 6.73E−05 |
| SEQ ID NO 77 | Hapmap55208-ss46526613 | 2/0.56 | 19.14 | 6.99E−05 |
| SEQ ID NO 78 | UA-IFASA-7062 | 14/28.50 | 19.12 | 7.05E−05 |
| SEQ ID NO 79 | Hapmap43556-BTA-33007 | 13/56.98 | 19.04 | 7.35E−05 |
| SEQ ID NO 80 | ARS-BFGL-NGS-26323 | 9/29.68 | 19.01 | 7.43E−05 |
| SEQ ID NO 81 | ARS-BFGL-NGS-52539 | 10/18.96 | 18.96 | 7.62E−05 |
| SEQ ID NO 82 | Hapmap43854-BTA-43847 | 18/56.40 | 18.93 | 7.76E−05 |
| SEQ ID NO 83 | ARS-BFGL-NGS-111520 | 15/76.24 | 18.83 | 8.14E−05 |
| SEQ ID NO 84 | Hapmap43873-BTA-50695 | 20/45.91 | 18.64 | 8.96E−05 |
| SEQ ID NO 85 | BTB-00617870 | 15/78.61 | 18.55 | 9.38E−05 |
| SEQ ID NO 86 | BTA-28297-no-rs | 10/19.03 | 18.47 | 9.75E−05 |
| SEQ ID NO 87 | BTA-61688-no-rs | 26/42.60 | 18.42 | 0.0001 |
| SEQ ID NO 88 | ARS-BFGL-NGS-112293 | 15/63.04 | 18.36 | 0.000103 |
| SEQ ID NO 89 | BTA-60642-no-rs | 25/8.65 | 18.09 | 0.000118 |
| SEQ ID NO 90 | ARS-BFGL-NGS-36892 | 17/67.75 | 17.91 | 0.000129 |
| SEQ ID NO 91 | BTB-00310653 | 7/46.58 | 17.68 | 0.000145 |
| SEQ ID NO 92 | Hapmap49429-BTA-107409 | 16/69.99 | 17.65 | 0.000147 |
| SEQ ID NO 93 | ARS-BFGL-NGS-17676 | 20/39.04 | 17.62 | 0.00015 |
| SEQ ID NO 94 | BTA-114108-no-rs | 1/26.10 | 17.58 | 0.000152 |
| SEQ ID NO 95 | Hapmap32845-BTA-152047 | 26/35.72 | 17.57 | 0.000153 |
| SEQ ID NO 96 | ARS-BFGL-NGS-36809 | 13/31.48 | 17.5 | 0.000159 |
| SEQ ID NO 97 | Hapmap38112-BTA-50631 | 20/42.72 | 17.35 | 0.00017 |
| SEQ ID NO 98 | ARS-BFGL-NGS-86252 | 23/16.59 | 17.15 | 0.000189 |
| SEQ ID NO 99 | ARS-BFGL-NGS-42452 | 7/65.74 | 17.09 | 0.000194 |
| SEQ ID NO 100 | Hapmap41054-BTA-67528 | 3/34.52 | 17.02 | 0.000201 |
| SEQ ID NO 101 | Hapmap48202-BTA-118947 | 20/30.16 | 17.02 | 0.000201 |
| SEQ ID NO 102 | BTB-01731152 | 17/28.15 | 16.95 | 0.000208 |
| SEQ ID NO 103 | BTB-01337853 | 12/66.70 | 16.73 | 0.000233 |

TABLE A-continued

SNPs Useful for Predicting An Increased Susceptibility
To Contracting Paratuberculosis

| | SNP_ID | BTA/Mb | Chi-squared | P-value |
|---|---|---|---|---|
| SEQ ID NO 104 | Hapmap56001-rs29023690 | 16/62.05 | 16.66 | 0.000241 |
| SEQ ID NO 105 | Hapmap55502-rs29014080 | 6/72.21 | 16.14 | 0.000313 |
| SEQ ID NO 106 | Hapmap38405-BTA-35996 | 14/18.90 | 16.11 | 0.000318 |
| SEQ ID NO 107 | Hapmap43792-BTA-122725 | 13/83.21 | 16.08 | 0.000323 |
| SEQ ID NO 108 | ARS-BFGL-NGS-55607 | 29/5.03 | 16.05 | 0.000327 |
| SEQ ID NO 109 | Hapmap48185-BTA-112403 | 24/27.36 | 16.01 | 0.000333 |
| SEQ ID NO 110 | BTA-119803-no-rs | 11/83.28 | 15.66 | 0.000397 |
| SEQ ID NO 111 | Hapmap49750-BTA-76652 | 6/72.25 | 15.43 | 0.000447 |
| SEQ ID NO 112 | Hapmap52400-rs29025316 | 7/54.59 | 15.39 | 0.000456 |
| SEQ ID NO 113 | BTA-121819-no-rs | 7/105.09 | 15.37 | 0.000459 |
| SEQ ID NO 114 | ARS-BFGL-NGS-100092 | 26/36.33 | 15.37 | 0.000459 |
| SEQ ID NO 115 | ARS-BFGL-NGS-23638 | 26/41.14 | 15.29 | 0.000478 |
| SEQ ID NO 116 | Hapmap43736-BTA-98788 | 13/26.26 | 15.21 | 0.000497 |
| SEQ ID NO 117 | ARS-BFGL-NGS-43032 | 16/14.39 | 15.18 | 0.000504 |
| SEQ ID NO 118 | ARS-BFGL-NGS-101723 | 10/11.22 | 15.14 | 0.000515 |
| SEQ ID NO 119 | BTB-01887959 | 22/9.23 | 15.13 | 0.000519 |
| SEQ ID NO 120 | Hapmap47541-BTA-22031 | 20/39.61 | 14.99 | 0.000556 |
| SEQ ID NO 121 | Hapmap39665-BTA-59836 | 25/26.31 | 14.83 | 0.000602 |
| SEQ ID NO 122 | ARS-BFGL-NGS-1808 | 14/83.04 | 14.8 | 0.00061 |
| SEQ ID NO 123 | ARS-BFGL-NGS-21527 | 25/25.75 | 14.76 | 0.000624 |
| SEQ ID NO 124 | UA-IFASA-4794 | 28/22.77 | 14.71 | 0.000638 |
| SEQ ID NO 125 | ARS-BFGL-NGS-76451 | 1/138.44 | 14.61 | 0.000674 |
| SEQ ID NO 126 | BTB-00360436 | 8/76.85 | 14.31 | 0.00078 |
| SEQ ID NO 127 | BTB-01790614 | 6/3.21 | 14.25 | 0.000806 |
| SEQ ID NO 128 | ARS-BFGL-NGS-86477 | 21/67.62 | 14.2 | 0.000826 |
| SEQ ID NO 129 | Hapmap25321-BTA-156840 | 22/9.37 | 14.17 | 0.000838 |
| SEQ ID NO 130 | BTB-00783271 | 20/41.21 | 13.76 | 0.00103 |
| SEQ ID NO 131 | Hapmap47083-BTA-71984 | 4/100.70 | 13.72 | 0.00105 |
| SEQ ID NO 132 | BTB-01092452 | 8/81.40 | 13.46 | 0.0012 |
| SEQ ID NO 133 | Hapmap48829-BTA-61554 | 26/39.68 | 13.41 | 0.00123 |
| SEQ ID NO 134 | BTA-19348-no-rs | 8/64.88 | 13.35 | 0.00126 |
| SEQ ID NO 135 | ARS-BFGL-NGS-33495 | 8/88.53 | 13.18 | 0.00137 |
| SEQ ID NO 136 | BTB-01475042 | 20/51.95 | 13.17 | 0.00138 |
| SEQ ID NO 137 | ARS-BFGL-NGS-113490 | 3/109.84 | 13.05 | 0.00147 |
| SEQ ID NO 138 | ARS-BFGL-NGS-32966 | 9/38.39 | 12.74 | 0.00171 |
| SEQ ID NO 139 | ARS-BFGL-NGS-2600 | 24/19.69 | 12.69 | 0.00175 |
| SEQ ID NO 140 | Hapmap51600-BTA-50467 | 20/36.77 | 12.66 | 0.00178 |
| SEQ ID NO 141 | BTB-01112664 | 2/19.39 | 12.64 | 0.0018 |
| SEQ ID NO 142 | UA-IFASA-1789 | 14/34.76 | 12.44 | 0.00199 |
| SEQ ID NO 143 | Hapmap45971-BTA-102151 | 11/69.73 | 11.88 | 0.00263 |
| SEQ ID NO 144 | ARS-BFGL-NGS-7597 | 4/102.25 | 11.48 | 0.00322 |
| SEQ ID NO 145 | ARS-BFGL-NGS-23298 | 19/60.94 | 11.2 | 0.00369 |
| SEQ ID NO 146 | ARS-BFGL-NGS-103845 | 7/56.99 | 11.19 | 0.00371 |
| SEQ ID NO 147 | Hapmap59876-rs29018046 | 2/14.00 | 11.08 | 0.00392 |
| SEQ ID NO 148 | ARS-BFGL-NGS-102130 | 24/41.61 | 10.89 | 0.00431 |
| SEQ ID NO 149 | BTA-72108-no-rs | 4/108.78 | 10.85 | 0.0044 |
| SEQ ID NO 150 | BTB-01839787 | 17/30.34 | 10.69 | 0.00478 |
| SEQ ID NO 151 | Hapmap56784-rs29012419 | 20/52.23 | 9.89 | 0.00714 |
| SEQ ID NO 152 | ARS-BFGL-NGS-84716 | 15/82.47 | 9.74 | 0.00767 |
| SEQ ID NO 153 | Hapmap43830-BTA-29180 | 13/82.90 | 9.73 | 0.00772 |
| SEQ ID NO 154 | ARS-BFGL-NGS-34254 | 5/27.55 | 9.48 | 0.00873 |
| SEQ ID NO 155 | ARS-BFGL-NGS-49057 | 3/72.95 | 9.42 | 0.00901 |
| SEQ ID NO 156 | Hapmap50205-BTA-107882 | 9/78.41 | 9.04 | 0.0109 |
| SEQ ID NO 157 | ARS-BFGL-NGS-18128 | 17/21.16 | 8.98 | 0.0112 |
| SEQ ID NO 158 | ARS-BFGL-NGS-21860 | 17/24.67 | 8.74 | 0.0127 |
| SEQ ID NO 159 | Hapmap40908-BTA-121388 | 23/6.69 | 8.67 | 0.0131 |
| SEQ ID NO 160 | BTA-111934-no-rs | 9/52.95 | 8.62 | 0.0134 |
| SEQ ID NO 161 | UA-IFASA-8351 | 23/36.28 | 8.6 | 0.0136 |
| SEQ ID NO 162 | ARS-BFGL-NGS-16677 | 29/37.34 | 8.28 | 0.0159 |
| SEQ ID NO 163 | BTA-27242-no-rs | 5/20.21 | 7.74 | 0.0209 |
| SEQ ID NO 164 | ARS-BFGL-NGS-109845 | 29/19.50 | 7.66 | 0.0217 |
| SEQ ID NO 165 | ARS-BFGL-NGS-118058 | 2/23.36 | 7.65 | 0.0218 |
| SEQ ID NO 166 | Hapmap58939-rs29011360 | 3/43.09 | 7.59 | 0.0224 |
| SEQ ID NO 167 | ARS-BFGL-NGS-106807 | 15/41.61 | 7.31 | 0.0259 |
| SEQ ID NO 168 | ARS-BFGL-NGS-74054 | 24/42.08 | 7.16 | 0.0279 |
| SEQ ID NO 169 | ARS-BFGL-NGS-53471 | 6/116.93 | 7.1 | 0.0287 |
| SEQ ID NO 170 | ARS-BFGL-NGS-112793 | 12/86.28 | 6.92 | 0.0314 |
| SEQ ID NO 171 | Hapmap55067-ss46526268 | 23/18.58 | 6.88 | 0.032 |
| SEQ ID NO 172 | Hapmap45550-BTA-32092 | 13/36.23 | 6.43 | 0.0402 |
| SEQ ID NO 173 | ARS-BFGL-NGS-75935 | 21/24.69 | 6.3 | 0.043 |
| SEQ ID NO 174 | BTA-100864-no-rs | 13/9.08 | 6.2 | 0.045 |
| SEQ ID NO 175 | ARS-BFGL-NGS-117518 | 17/28.09 | 6.2 | 0.0451 |
| SEQ ID NO 176 | Hapmap26742-BTA-156593 | 17/42.53 | 6.1 | 0.0472 |
| SEQ ID NO 177 | ARS-BFGL-NGS-39305 | 13/4.74 | 5.71 | 0.0575 |
| SEQ ID NO 178 | Hapmap60394-rs29020827 | 13/71.23 | 5.54 | 0.0627 |

TABLE A-continued

SNPs Useful for Predicting An Increased Susceptibility To Contracting Paratuberculosis

| | SNP_ID | BTA/Mb | Chi-squared | P-value |
|---|---|---|---|---|
| SEQ ID NO 179 | UA-IFASA-2293 | 20/59.45 | 5.47 | 0.0648 |
| SEQ ID NO 180 | ARS-BFGL-NGS-114525 | 7/53.19 | 5.28 | 0.0714 |
| SEQ ID NO 181 | BTB-01250562 | 7/82.51 | 5.01 | 0.0816 |
| SEQ ID NO 182 | Hapmap43880-BTA-54826 | 22/52.10 | 4.8 | 0.0909 |
| SEQ ID NO 183 | ARS-BFGL-NGS-115608 | 21/24.71 | 4.79 | 0.0912 |
| SEQ ID NO 184 | BTA-54617-no-rs | 22/45.42 | 4.55 | 0.103 |
| SEQ ID NO 185 | BTB-01011603 | 29/21.15 | 4.45 | 0.108 |
| SEQ ID NO 186 | ARS-BFGL-NGS-102205 | 2/94.47 | 4.05 | 0.132 |
| SEQ ID NO 187 | ARS-BFGL-NGS-24141 | 9/91.47 | 3.94 | 0.139 |
| SEQ ID NO 188 | ARS-BFGL-NGS-39985 | 13/71.17 | 3.83 | 0.147 |
| SEQ ID NO 189 | ARS-BFGL-NGS-101621 | 13/76.41 | 3.61 | 0.164 |
| SEQ ID NO 190 | ARS-BFGL-NGS-23356 | 13/5.26 | 3.6 | 0.165 |
| SEQ ID NO 191 | ARS-BFGL-NGS-55380 | 16/22.06 | 3.34 | 0.188 |
| SEQ ID NO 192 | Hapmap51102-BTA-97964 | 6/54.36 | 2.87 | 0.238 |
| SEQ ID NO 193 | BTA-34427-no-rs | 2/112.67 | 2.8 | 0.247 |
| SEQ ID NO 194 | ARS-BFGL-NGS-79435 | 29/16.50 | 1.23 | 0.54 |
| SEQ ID NO 195 | BTB-01195060 | 7/54.86 | 0.74 | 0.69 |
| SEQ ID NO 196 | ARS-BFGL-NGS-64241 | 9/76.67 | 0.74 | 0.691 |
| SEQ ID NO 197 | ARS-BFGL-NGS-3747 | 27/37.86 | 0.39 | 0.822 |

In various embodiments of the collections or the methods below, the SNPs preferably comprise one or more of the SNPs listed in Table B.

TABLE B

Preferred SNPs Useful for Predicting an Increased Susceptibility To Contracting Paratuberculosis

| | SNP_ID | BTA/Mb |
|---|---|---|
| SEQ ID NO 4 | ARS-BFGL-BAC-13827 | 13/33.53 |
| SEQ ID NO 8 | Hapmap51130-BTA-105627 | 23/32.11 |
| SEQ ID NO 12 | BTA-13956-no-rs | 14/64.31 |
| SEQ ID NO 14 | BTB-00261837 | 6/66.68 |
| SEQ ID NO 15 | ARS-BFGL-NGS-16165 | 16/64.91 |
| SEQ ID NO 16 | ARS-BFGL-NGS-114768 | 26/38.92 |
| SEQ ID NO 25 | Hapmap51169-BTA-122103 | 7/56.17 |
| SEQ ID NO 29 | Hapmap42075-BTA-114094 | 16/69.88 |
| SEQ ID NO 34 | BTA-15204-no-rs | 20/34.74 |
| SEQ ID NO 35 | BTA-61435-no-rs | 26/36.89 |
| SEQ ID NO 36 | Hapmap51346-BTA-89239 | 9/6.17 |
| SEQ ID NO 37 | Hapmap49609-BTA-43790 | 18/51.49 |
| SEQ ID NO 41 | ARS-BFGL-NGS-31976 | 13/71.05 |
| SEQ ID NO 45 | Hapmap56950-ss46526304 | 3/114.08 |
| SEQ ID NO 53 | UA-IFASA-8974 | 20/31.97 |
| SEQ ID NO 57 | ARS-BFGL-NGS-101744 | 15/69.30 |
| SEQ ID NO 60 | ARS-BFGL-NGS-115504 | 25/21.17 |
| SEQ ID NO 61 | BTB-00780124 | 20/35.88 |
| SEQ ID NO 62 | ARS-BFGL-NGS-101940 | 21/19.58 |
| SEQ ID NO 71 | ARS-BFGL-NGS-29032 | 16/61.38 |
| SEQ ID NO 74 | BTA-100341-no-rs | 26/34.88 |
| SEQ ID NO 76 | ARS-BFGL-NGS-41833 | 20/66.58 |
| SEQ ID NO 78 | UA-IFASA-7062 | 14/28.50 |
| SEQ ID NO 85 | BTB-00617870 | 15/78.61 |
| SEQ ID NO 86 | BTA-28297-no-rs | 10/19.03 |
| SEQ ID NO 89 | BTA-60642-no-rs | 25/8.65 |
| SEQ ID NO 95 | Hapmap32845-BTA-152047 | 26/35.72 |
| SEQ ID NO 96 | ARS-BFGL-NGS-36809 | 13/31.48 |
| SEQ ID NO 102 | BTB-01731152 | 17/28.15 |
| SEQ ID NO 112 | Hapmap52400-rs29025316 | 7/54.59 |
| SEQ ID NO 128 | ARS-BFGL-NGS-86477 | 21/67.62 |
| SEQ ID NO 129 | Hapmap25321-BTA-156840 | 22/9.37 |
| SEQ ID NO 133 | Hapmap48829-BTA-61554 | 26/39.68 |
| SEQ ID NO 141 | BTB-01112664 | 2/19.39 |
| SEQ ID NO 144 | ARS-BFGL-NGS-7597 | 4/102.25 |
| SEQ ID NO 149 | BTA-72108-no-rs | 4/108.78 |
| SEQ ID NO 150 | BTB-01839787 | 17/30.34 |
| SEQ ID NO 154 | ARS-BFGL-NGS-34254 | 5/27.55 |
| SEQ ID NO 162 | ARS-BFGL-NGS-16677 | 29/37.34 |
| SEQ ID NO 164 | ARS-BFGL-NGS-109845 | 29/19.50 |
| SEQ ID NO 171 | Hapmap55067-ss46526268 | 23/18.58 |
| SEQ ID NO 173 | ARS-BFGL-NGS-75935 | 21/24.69 |
| SEQ ID NO 176 | Hapmap26742-BTA-156593 | 17/42.53 |
| SEQ ID NO 177 | ARS-BFGL-NGS-39305 | 13/4.74 |
| SEQ ID NO 183 | ARS-BFGL-NGS-115608 | 21/24.71 |
| SEQ ID NO 185 | BTB-01011603 | 29/21.15 |
| SEQ ID NO 187 | ARS-BFGL-NGS-24141 | 9/91.47 |
| SEQ ID NO 190 | ARS-BFGL-NGS-23356 | 13/5.26 |
| SEQ ID NO 191 | ARS-BFGL-NGS-55380 | 16/22.06 |
| SEQ ID NO 192 | Hapmap51102-BTA-97964 | 6/54.36 |
| SEQ ID NO 193 | BTA-34427-no-rs | 2/112.67 |

Still other SNPs that are useful in connection herewith include various SNPs on BTA20, particularly SNPs within the PTGER4 region, and BTA7, particularly SNPs within the IRGM region.

In one embodiment, the collection comprises a group of SNPs comprising one or more of those give in Table A. In another embodiment, the collection of polynucleotides comprises each of the foregoing SNPs. In one presently preferred embodiment, the following table (Table C) using exemplar SNPs can be used to construct a polynomial equation for predicting the association of a particular SNP or collection of SNPs with the trait of an increased susceptibility to contracting paratuberculosis.

TABLE C

Factors for predicting an increased susceptibility to contracting paratuberculosis using specific SNP
Table C. Coefficients for SNPs in final model: P < 0.01 threshold.

| Parameter | Estimate | SE[1] | P-value |
|---|---|---|---|
| Intercept | 5.395 | 1.074 | $5.05 \times 10^{-7}$ |

| Parameter | Estimate 0 vs 2 | SE[1] | P-value | Estimate 1 vs 2 | SE[1] | P-value | 0/1/2 |
|---|---|---|---|---|---|---|---|
| BTB-01342789 | −0.140 | 0.256 | $5.85 \times 10^{-1}$ | 0.671 | 0.260 | $9.85 \times 10^{-3}$ | TT/TC/CC |
| BTA-114108-no-rs | −0.200 | 0.282 | $4.77 \times 10^{-1}$ | −0.543 | 0.184 | $3.23 \times 10^{-3}$ | AA/AC/CC |
| BTB-01112664 | 1.138 | 0.327 | $5.04 \times 10^{-4}$ | −0.397 | 0.195 | $4.19 \times 10^{-2}$ | TT/TG/GG |
| ARS-BFGL-NGS-118058 | 0.444 | 0.187 | $1.73 \times 10^{-2}$ | 0.152 | 0.148 | $3.06 \times 10^{-1}$ | AA/AG/AG |
| Hapmap58939-rs29011360 | 0.875 | 0.289 | $2.45 \times 10^{-3}$ | −0.196 | 0.191 | $3.05 \times 10^{-1}$ | AA/AG/AG |
| BTB-01278461 | −1.393 | 0.460 | $2.48 \times 10^{-3}$ | −0.086 | 0.481 | $8.59 \times 10^{-1}$ | TT/TC/CC |
| BTA-72108-no-rs | −0.525 | 0.355 | $1.39 \times 10^{-1}$ | −1.536 | 0.406 | $1.57 \times 10^{-4}$ | TT/TC/CC |
| ARS-BFGL-NGS-34254 | −0.016 | 0.164 | $9.24 \times 10^{-1}$ | −0.541 | 0.165 | $1.06 \times 10^{-3}$ | TT/TC/CC |
| BTB-00261837 | 0.755 | 0.211 | $3.35 \times 10^{-4}$ | 0.158 | 0.155 | $3.08 \times 10^{-1}$ | TT/TC/CC |
| ARS-BFGL-NGS-103845 | −0.183 | 0.180 | $3.09 \times 10^{-1}$ | 0.514 | 0.148 | $5.17 \times 10^{-4}$ | TT/TC/CC |
| Hapmap41410-BTA-104176 | −1.821 | 0.943 | $5.35 \times 10^{-2}$ | −0.121 | 0.961 | $9.00 \times 10^{-1}$ | TT/TC/CC |
| ARS-BFGL-NGS-32966 | 0.984 | 0.573 | $8.61 \times 10^{-2}$ | −0.111 | 0.314 | $7.24 \times 10^{-1}$ | AA/AG/AG |
| ARS-BFGL-NGS-64241 | 0.828 | 0.368 | $2.42 \times 10^{-2}$ | 0.021 | 0.218 | $9.23 \times 10^{-1}$ | TT/TC/CC |
| BTA-28297-no-rs | −0.965 | 0.231 | $3.06 \times 10^{-5}$ | −0.238 | 0.231 | $3.03 \times 10^{-1}$ | GG/GC/CC |
| Hapmap57166-rs29020401 | −0.773 | 0.207 | $1.87 \times 10^{-4}$ | 0.149 | 0.219 | $4.98 \times 10^{-1}$ | AA/AG/AG |
| Hapmap43556-BTA-33007 | −0.452 | 0.252 | $7.30 \times 10^{-2}$ | 0.613 | 0.284 | $3.05 \times 10^{-2}$ | AA/AG/AG |
| ARS-BFGL-NGS-32123 | −0.092 | 0.179 | $6.08 \times 10^{-1}$ | 0.666 | 0.152 | $1.10 \times 10^{-5}$ | TT/TG/GG |
| ARS-BFGL-NGS-55380 | −0.817 | 0.169 | $1.32 \times 10^{-6}$ | −0.140 | 0.159 | $3.78 \times 10^{-1}$ | AA/AG/AG |
| BTA-116871-no-rs | 0.699 | 0.183 | $1.33 \times 10^{-4}$ | −0.941 | 0.157 | $2.26 \times 10^{-9}$ | TT/TC/CC |
| Hapmap26742-BTA-156593 | 1.085 | 0.299 | $2.82 \times 10^{-4}$ | 0.099 | 0.311 | $7.51 \times 10^{-1}$ | AA/AG/AG |
| Hapmap49609-BTA-43790 | −0.363 | 0.170 | $3.25 \times 10^{-2}$ | −0.532 | 0.162 | $1.06 \times 10^{-3}$ | AA/AG/AG |
| UA-IFASA-8974 | 0.709 | 0.192 | $2.13 \times 10^{-4}$ | −0.683 | 0.155 | $1.10 \times 10^{-5}$ | AA/AC/CC |
| ARS-BFGL-NGS-41833 | 0.333 | 0.245 | $1.74 \times 10^{-1}$ | −0.582 | 0.172 | $7.08 \times 10^{-4}$ | TT/TG/GG |
| ARS-BFGL-NGS-75935 | 0.399 | 0.198 | $4.37 \times 10^{-2}$ | 0.714 | 0.208 | $5.79 \times 10^{-4}$ | TT/TC/CC |
| Hapmap54042-ss46526396 | 1.278 | 0.216 | $3.30 \times 10^{-9}$ | −0.250 | 0.155 | $1.07 \times 10^{-1}$ | TT/TC/CC |
| Hapmap51130-BTA-105627 | −0.569 | 0.207 | $6.04 \times 10^{-3}$ | −0.165 | 0.152 | $2.79 \times 10^{-1}$ | AA/AG/AG |
| BTA-60642-no-rs | −0.768 | 0.194 | $7.19 \times 10^{-5}$ | −0.196 | 0.194 | $3.13 \times 10^{-1}$ | AA/AG/AG |
| ARS-BFGL-NGS-115504 | 0.884 | 0.275 | $1.28 \times 10^{-3}$ | −0.003 | 0.178 | $9.86 \times 10^{-1}$ | AA/AG/AG |
| BTA-100341-no-rs | 0.267 | 0.188 | $1.56 \times 10^{-1}$ | 0.682 | 0.153 | $8.37 \times 10^{-6}$ | TT/TG/GG |
| ARS-BFGL-NGS-109845 | 0.597 | 0.180 | $9.27 \times 10^{-4}$ | −0.134 | 0.152 | $3.79 \times 10^{-1}$ | TT/TC/CC |

[1]Standard error of coefficient estimate.

In one embodiment, the collection comprises a group of SNPs comprising one or more of those give in Table B. In another embodiment, the collection of polynucleotides comprises each of the foregoing SNPs. In one presently preferred embodiment, the following table (Table D) using exemplar SNPs can be used to construct a polynomial equation for predicting the association of a particular SNP or collection of SNPs with the trait of an increased susceptibility to contracting paratuberculosis.

TABLE D

Factors for predicting an increased susceptibility to contracting paratuberculosis using specific SNP
Table D. Coefficients for SNPs in final model: P < 0.001 threshold.

| Parameter | Estimate | SE[1] | P-value |
|---|---|---|---|
| Intercept | 5.395 | 1.074 | $5.05 \times 10^{-7}$ |

| Parameter | Estimate 0 vs 2 | SE[1] | P-value | Estimate 1 vs 2 | SE[1] | P-value | 0/1/2 |
|---|---|---|---|---|---|---|---|
| BTA-114108-no-rs | −0.274 | 0.248 | $2.70 \times 10^{-1}$ | −0.366 | 0.158 | $2.10 \times 10^{-2}$ | AA/AC/CC |
| BTB-01112664 | 1.045 | 0.264 | $7.51 \times 10^{-5}$ | −0.357 | 0.161 | $2.61 \times 10^{-2}$ | TT/TG/GG |
| ARS-BFGL-NGS-118058 | 0.392 | 0.152 | $9.93 \times 10^{-3}$ | 0.271 | 0.126 | $3.09 \times 10^{-2}$ | AA/AG/AG |
| BTB-01278461 | −1.326 | 0.496 | $7.51 \times 10^{-3}$ | 0.174 | 0.513 | $7.34 \times 10^{-1}$ | TT/TC/CC |
| BTA-72108-no-rs | −0.396 | 0.280 | $1.57 \times 10^{-1}$ | −1.333 | 0.325 | $4.19 \times 10^{-5}$ | TT/TC/CC |
| BTB-00261837 | 0.860 | 0.181 | $2.09 \times 10^{-6}$ | 0.027 | 0.129 | $8.37 \times 10^{-1}$ | TT/TC/CC |
| Hapmap41410-BTA-104176 | −1.751 | 0.900 | $5.16 \times 10^{-2}$ | −0.069 | 0.913 | $9.40 \times 10^{-1}$ | TT/TC/CC |
| ARS-BFGL-NGS-32966 | 1.114 | 0.467 | $1.70 \times 10^{-2}$ | −0.167 | 0.257 | $5.15 \times 10^{-1}$ | AA/AG/AG |
| Hapmap57166-rs29020401 | −0.498 | 0.164 | $2.38 \times 10^{-3}$ | 0.459 | 0.177 | $9.53 \times 10^{-3}$ | AA/AG/AG |
| ARS-BFGL-NGS-32123 | −0.175 | 0.149 | $2.38 \times 10^{-1}$ | 0.521 | 0.125 | $3.13 \times 10^{-5}$ | TT/TG/GG |
| ARS-BFGL-NGS-55380 | −0.769 | 0.142 | $6.31 \times 10^{-8}$ | −0.043 | 0.130 | $7.40 \times 10^{-1}$ | AA/AG/AG |
| BTA-116871-no-rs | 0.649 | 0.154 | $2.42 \times 10^{-5}$ | −0.817 | 0.131 | $4.44 \times 10^{-10}$ | TT/TC/CC |
| UA-IFASA-8974 | 0.644 | 0.153 | $2.59 \times 10^{-5}$ | −0.671 | 0.129 | $1.90 \times 10^{-7}$ | AA/AC/CC |
| Hapmap54042-ss46526396 | 1.021 | 0.185 | $3.68 \times 10^{-8}$ | −0.290 | 0.133 | $2.93 \times 10^{-2}$ | AA/AG/AG |
| Hapmap51130-BTA-105627 | −0.346 | 0.175 | $4.74 \times 10^{-2}$ | −0.194 | 0.130 | $1.35 \times 10^{-1}$ | AA/AG/AG |
| ARS-BFGL-NGS-115504 | 1.237 | 0.234 | $1.20 \times 10^{-7}$ | −0.158 | 0.151 | $2.93 \times 10^{-1}$ | AA/AG/AG |

TABLE D-continued

Factors for predicting an increased susceptibility to contracting paratuberculosis using specific SNP
Table D. Coefficients for SNPs in final model: P < 0.001 threshold.

| BTA-100341-no-rs | 0.474 | 0.160 | $2.98 \times 10^{-3}$ | 0.384 | 0.125 | $2.19 \times 10^{-3}$ | TT/TG/GG |
| ARS-BFGL-NGS-109845 | 0.748 | 0.152 | $8.37 \times 10^{-7}$ | −0.169 | 0.129 | $1.89 \times 10^{-1}$ | TT/TC/CC |

[1] Standard error of coefficient estimate

In another of its several aspects, this disclosure provides for methods of detecting sequences in a genome that provide an estimate of an increased susceptibility to contracting paratuberculosis probability or which have predictive value regarding an increased susceptibility to contracting paratuberculosis likelihood. In one embodiment, methods for estimating the likelihood of an increased susceptibility to contracting paratuberculosis in one or more members of a cattle population are provided. The methods generally comprise the steps of 1) providing a collection of one or more polynucleotides, each of which is at least partially complementary to a sequence in a cow genome, comprising at least one sequence that is quantitatively associated with an increased susceptibility to contracting paratuberculosis with statistical significance of at least $p \leq 0.01$;
2) using the collection to determine the presence or absence of sequences complementary to one or more polynucleotides from the collection in one or more members of the cattle population genome, wherein the presence or absence of the complementary sequences is quantitatively associated with the trait of an increased susceptibility to contracting paratuberculosis in a cattle population; and
3) estimating the likelihood of an increased susceptibility to contracting paratuberculosis based on the results of step 2).

The method, as the skilled artisan will appreciate, encompass use of collections of polynucleotides, for example, as described above, which are useful for detecting the presence or absence of sequences in a genome that are predictive of an increased susceptibility to contracting paratuberculosis. In one embodiment, the estimating step comprises a laboratory analysis. In such embodiments, the method comprises a statistical calculation. In other embodiments, the method comprises a field test. In many such embodiments, preferred tests are conveniently used to provide a threshold estimate or a visual indicator of acceptability. Preferably no actual statistical calculation is required for such field tests. Such tests may require the use of a chart, reader or other device to provide a measurement of an increased susceptibility to contracting paratuberculosis rate, or other useful measurement or result that reflects the likelihood of an increased susceptibility to contracting paratuberculosis.

Preferably, the methods provided herein feature a collection of polynucleotides that comprises at least one sequence that is quantitatively associated with an increased susceptibility to contracting paratuberculosis with statistical significance of at least $p \leq 0.01$. In other embodiments, the collection comprises at least one sequence that is quantitatively associated with an increased susceptibility to contracting paratuberculosis with statistical significance of at least $p \leq 0.005$. Most preferred are methods wherein the collection comprises at least one sequence that is quantitatively associated with an increased susceptibility to contracting paratuberculosis with statistical significance of at least $p \leq 0.001$.

The methods preferably are useful for estimating breeding value in cattle, thus preferably feature a collection of polynucleotides that is useful for estimating breeding value in cattle.

In various embodiments, the collection is useful for detecting the presence or absence of one allele of a SNP in the cow genome. Preferably, at least one of the polynucleotides in the collection is complementary to a sequence located on bovine chromosome 20 (BTA20). In another embodiment, at least one of the polynucleotides in the collection is complementary to a sequence located on bovine chromosome 26 (BTA26). In another embodiment, at least one of the polynucleotides in the collection is complementary to a sequence located on bovine chromosome 13 (BTA13). In another embodiment, at least one of the polynucleotides in the collection is complementary to a sequence located on bovine chromosome 16 (BTA16). In another embodiment, at least one of the polynucleotides in the collection is complementary to a sequence located on bovine chromosome 21 (BTA21).

In certain embodiments of the methods, at least one of the polynucleotides in the collection is complementary to a sequence that maps between 4-71 Mb of BTA13. In various embodiments, the collection comprises one or more polynucleotides complementary to a sequence that maps at either of 4-6 Mb, 31-34 Mb or 70-72 Mb of BTA13.

In certain embodiments of the methods, at least one of the polynucleotides in the collection is complementary to a sequence that maps between 21-70 Mb of BTA16. In various embodiments, the collection comprises one or more polynucleotides complementary to a sequence that maps at either of 21-23 Mb or 60-70 Mb of BTA16.

In certain embodiments of the methods, at least one of the polynucleotides in the collection is complementary to a sequence that maps between 31-67 Mb of BTA20. Especially preferred are particular regions of chromosome 20, including those that are near or encode certain genes. In various embodiments, the collection comprises one or more polynucleotides complementary to a sequence that maps on BTA20 at either of 31-35 Mb or 65-68 Mb of BTA20. In a currently preferred embodiment, at least one of the polynucleotides is complementary to a sequence that maps between 31-35 Mb of BTA20.

In certain embodiments of the methods, at least one of the polynucleotides in the collection is complementary to a sequence that maps between 19-68 Mb of BTA7. In various embodiments, the collection comprises one or more polynucleotides complementary to a sequence that maps at either of 19-25 Mb or 61-69 Mb of BTA7.

In certain embodiments of the methods, at least one of the polynucleotides in the collection is complementary to a sequence that maps between 34-40 Mb of BTA26. Also useful are polynucleotides that can identify the presence or absence of sequences which map to various overlapping or more specific locations, as set forth in the Examples below.

In a presently preferred method, at least one of the polynucleotides in the collection is complementary to a sequence located in a genomic sequence for Prostaglandin E receptor 4 ("PTGER4"). In another presently preferred method, at least one of the polynucleotides in the collection is complementary to a sequence located in a genomic sequence IRGM.

In other embodiments useful with the methods, the collection comprises at least one polynucleotide useful for detecting one or more of the SNPs: SEQ ID NO: 3; SEQ ID NO: 4; SEQ ID NO: 5; SEQ ID NO: 6; SEQ ID NO: 9; SEQ ID NO: 10; SEQ ID NO: 11; SEQ ID NO: 13; SEQ ID NO: 14; SEQ ID NO: 16; SEQ ID NO: 17; SEQ ID NO: 20; SEQ ID NO: 21; SEQ ID NO: 24; SEQ ID NO: 25; SEQ ID NO: 26; SEQ ID NO: 34; SEQ ID NO: 37; SEQ ID NO: 41; SEQ ID NO: 42; SEQ ID NO: 46; SEQ ID NO: 47; SEQ ID NO: 48; SEQ ID NO: 51; SEQ ID NO: 55; SEQ ID NO: 57; SEQ ID NO: 59; SEQ ID NO: 60; SEQ ID NO: 61; SEQ ID NO: 66.

In currently preferred embodiment embodiments useful with the methods, the collection comprises at least one polynucleotide useful for detecting one or more of the SNPs: SEQ ID NO: 4; SEQ ID NO: 5; SEQ ID NO: 6; SEQ ID NO: 10; SEQ ID NO: 11; SEQ ID NO: 14; SEQ ID NO: 17; SEQ ID NO: 20; SEQ ID NO: 25; SEQ ID NO: 34; SEQ ID NO: 37; SEQ ID NO: 41; SEQ ID NO: 47; SEQ ID NO: 55; SEQ ID NO: 57; SEQ ID NO: 60; SEQ ID NO: 61; SEQ ID NO: 66.

The collection can also feature at least one polynucleotide that is in high LD to any of the above SNPs useful for detecting one or more of the SNPs. These polynucleotides would be able to be determined by an average practitioner skilled in the art once the practitioner knows the above-given SNPs.

In yet another of its several aspects, this disclosure provides kits that comprise one or more of the collections of polynucleotides useful for detecting sequences in a genome that are quantitatively associated with an increased susceptibility to contracting paratuberculosis, and instructions for use of the collection(s) for estimating breeding value or predicting the likelihood of an increased susceptibility to contracting paratuberculosis.

These and other aspects of the invention will be further illustrated by the following working examples which are included to augment, not limit the understanding and communication of the invention, as expressed in the appended claims.

Examples

The invention can be further illustrated by the following examples, although it will be understood that these examples included merely for purposes of illustrating and better describing certain aspects of what is disclosed herein. The examples do not limit the scope of the invention unless otherwise specifically indicated.

Two resource populations of approximately 5,000 cows each were used to identify genomic regions associated with susceptibility to infection by MAP. The first population (Population 1) consisted primarily of twelve Holstein paternal half-sib families of daughters of sires heavily used within the breed. Cows were specifically chosen to be in second or later lactation to increase the likelihood of identifying cows manifesting evidence of infection. The second resource population consisted of cows from six Holstein herds in Wisconsin. Blood samples were obtained from all cows in these herds over a period of 15 months in 2006-07. Phenotype for MAP infection in Population 1 was based on both fecal culture of MAP and evidence of antibody titer to MAP as based on an ELISA test. Samples had been previously tested using the IDEXX ELISA (Gonda et al., 2006), but were re-tested for this study using a more recently developed ELISA with higher sensitivity (Shin et al., 2008). Phenotypes for Population 2 were ELISA results, also with the recently developed, higher sensitivity test.

Samples from both populations were genotyped with bead chips. Animals with fewer than 95% successfully scored genotypes and markers that were successfully scored for fewer than 90% of the samples in either of the two resource populations were removed prior to statistical analyses. In addition, SNPs with unknown genomic location or with minor allele frequencies below 5% were not included in analyses. After exclusion for these various reasons, a total of 35,772 SNPs remained.

Given the known paternal half-sib family structure in Population 1, female samples were checked for paternity relative to potential sires using a subset of 200 SNPs with high minor allele frequency. Of 233 females, 205 were verified as daughters of project sires.

Analysis of data from Population 1 accounted for the paternal half-sib family structure in the population. Inheritance of paternal and maternal haplotypes in Population 1 was determined using a Fortran program (de Roos et al., 2008) that compared sire and offspring genotypes. Paternally inherited haplotypes at each marker bracket were evaluated for deviation from a frequency of 0.5 expected under the null hypothesis of no linkage using a z test calculated as:

$$z = \frac{\hat{p} - 0.5}{\sqrt{\hat{p}\hat{q} * (1/n)}},$$

where p is the frequency of sire haplotype 1, q is 1-p and n is the number of offspring in the family. To combine linkage results across families, p-value for the 12 families were multiplied, and then compared with an empirical distribution of corresponding values obtained by simulation. For the simulation, 12 families of the same size as those in Population 1 were created with sire haplotypes one and two generated under the assumption of equal frequency (null hypothesis). The simulation was repeated one million times to generate an empirical distribution of results for determination of an empirical p-value.

Frequency of maternally inherited alleles from daughters in paternal half-sib families were used for a case-control analysis, in combination with allele frequency estimates from 28 positive cows which were not daughters of the 12 project sires. Maternally inherited allele frequencies were estimated using a single locus, maximum likelihood estimator. The control samples for the case-control analysis were not matching negatives, but rather an extensive sample of Holstein bulls used as artificial insemination (AI) sires. Bull genotype data was obtained from the USDA and Cooperative Dairy DNA Repository (CDDR) cooperators. Bulls were chosen based on birth year to represent population allele frequencies corresponding to the alleles from the MAP infection-positive cows. For Population 1, the sires selected were born between 1979 and 1990 and totaled 748. For Population 2, the selected sires were born between 1987 and 1998 and totaled 2,937. For combined analyses of Populations 1 and 2, the combined set of sires spanned birth years from 1979 to 1998 and totaled 3,271. These sire birth years were chosen considering the average difference in birth year of sires and daughters (9 yrs.) and average difference in age of dams and daughters (3.5 yrs.). Additionally, for Population 1, the alleles considered from cases are those inherited from the cows' mothers. These sire samples provided an accurate estimate of Holstein population allele frequency for comparison with the allele frequency observed in positive cows. The two separate pieces of information (linkage, case-control i.e. linkage disequilibrium) were subsequently combined to yield a combined linkage-linkage disequilibrium result.

Allele frequencies were estimated directly in the second population without consideration of family structure, owing to the use of a large number of sires within the six commercial herds. Genotype data from Population 2 was examined for evidence of stratification or clustering using multidimensional scaling plots and IBS clustering as implemented in PLINK v1.05 (Purcell et al., 2007). There was no evidence of stratification or clustering related to herd or otherwise. As in the analysis of data from Population 1, allele frequency estimates from affected cows were compared with allele frequencies estimated from 6,283 US Holstein AI sires. In contrast to Population 1, where allele frequencies were estimated using maternally inherited haplotypes, and comparison of genotype frequencies with the control group was not feasible, it was also possible in Population 2 to test differences in genotype frequency with the exception of the X chromosome.

A combined analysis across populations was conducted by calculating a weighted average for allele frequency using the estimates obtained as described above for the two populations. The combined allele frequency estimates were compared as described above with population allele frequency estimates based on genotypes from 3,271 Holstein AI sires. This result was combined with results from the linkage analysis from population 1 for an overall linkage-linkage disequilibrium analysis.

The most significant markers from separate and combined case-control and linkage-linkage disequilibrium analyses (n=1,356) were used in logistic regression analysis to identify a subset of markers which could be used in genomic selection. The data set was comprised of the 521 cows from resource populations 1 and 2 positive for MAP infection, as described above, and the 3,271 Holstein AI sires. These 3,792 samples were randomly assigned to ten groups. For model development and cross-validation, nine of the ten groups were combined to comprise a training data set, and the model developed from the training data set was applied in prediction using the remaining group or testing data set. Model efficacy was evaluated by determining percent concordance. A pair of observations with different observed responses (case vs. control) was concordant if the observation with the lower ordered response value had a lower predicted score than the observation with the higher ordered response value. This analysis was repeated for all ten possible combinations. Models were constructed using a forward-stepwise approach with a minimum probability for SNP entry of P<0.005 and a minimum probability for continued inclusion in the model of P<0.001. SNPs chosen for each of the 10 training sets were tabulated, and SNPs appearing in models for at least half of the training sets were used in a final model, with model coefficients estimated from the full data set.

Given the limited family and population size, power of the across-family linkage analysis of Population 1 was relatively low. Additionally, the modest family sizes likely created some errors in haplotype estimation leading to some spurious results (e.g. the strong but isolated linkage result near the telomeric end of BTA5). However, a strong and consistent linkage signal ($p<1\times10^{-3}$) was observed on chromosome 20 (FIG. 1), strengthening and refining a previous observation based on a subset of the population and within-family linkage analysis of microsatellite marker data (Gonda et al., 2007). Suggestive individual SNP associations ($p<5\times10^{-5}$) were observed in multiple genomic locations including BTA6, 7, 8, 11, 13, 17, 18, 22, 27, 28 and X. However, no individual marker associations surpassed a more stringent level of $1\times10^{-7}$ adopted for significant linkage.

Figure 2:
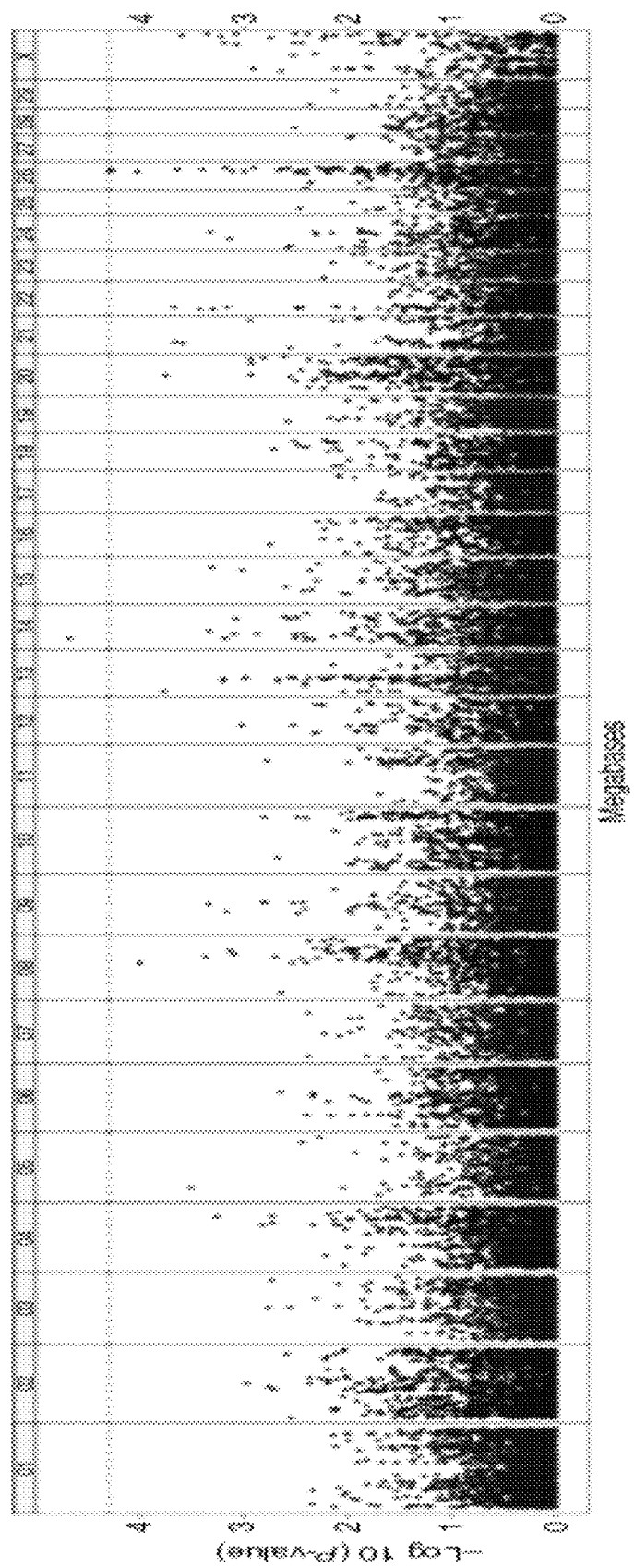
FIG. 2: Results of whole genome scan of Population 2 for genetic marker association with susceptibility to infection of cattle by MAP. Vertical panels denote individual chromosomes as indicated at the top of each panel. Each point represents the –log 10 of the P-value (y-axis) from tests of difference in allelic (top; "A") and genotypic (bottom; "G";) frequencies for case (cows ELISA-positive for MAP infection) and control (Holstein artificial insemination sires, as described in the text). Minus $Log_{10}$ (P-value) is plotted relative to genomic location of the SNP marker (x-axis). A total of 35, 772 polymorphic SNP markers were included in the analysis. The dashed and dotted lines represent p-values of $5\times10^{-5}$ and $1\times10^{-7}$, respectively, corresponding to suggestive and significant results.

The pattern of results from allelic and genotypic tests of Population 2 were generally consistent, though the specific markers with strongest association varied between tests (FIG. 2). Markers on all chromosomes surpassed a threshold of $P<5\times10^{-5}$ for either test while at a higher threshold ($1\times10^{-7}$) significance was observed on BTA1, 2, 3, 4, 6, 7, 9, 10, 11, 12, 13, 16, 17, 21, 22, 25, 29 and X. In general, results from analysis of Population 2 were more significant than Population 1, owing in part to the larger number of bulls used as a control group. Correspondence between the most significant associations from Populations 1 and 2 was not striking.

Figure 3:
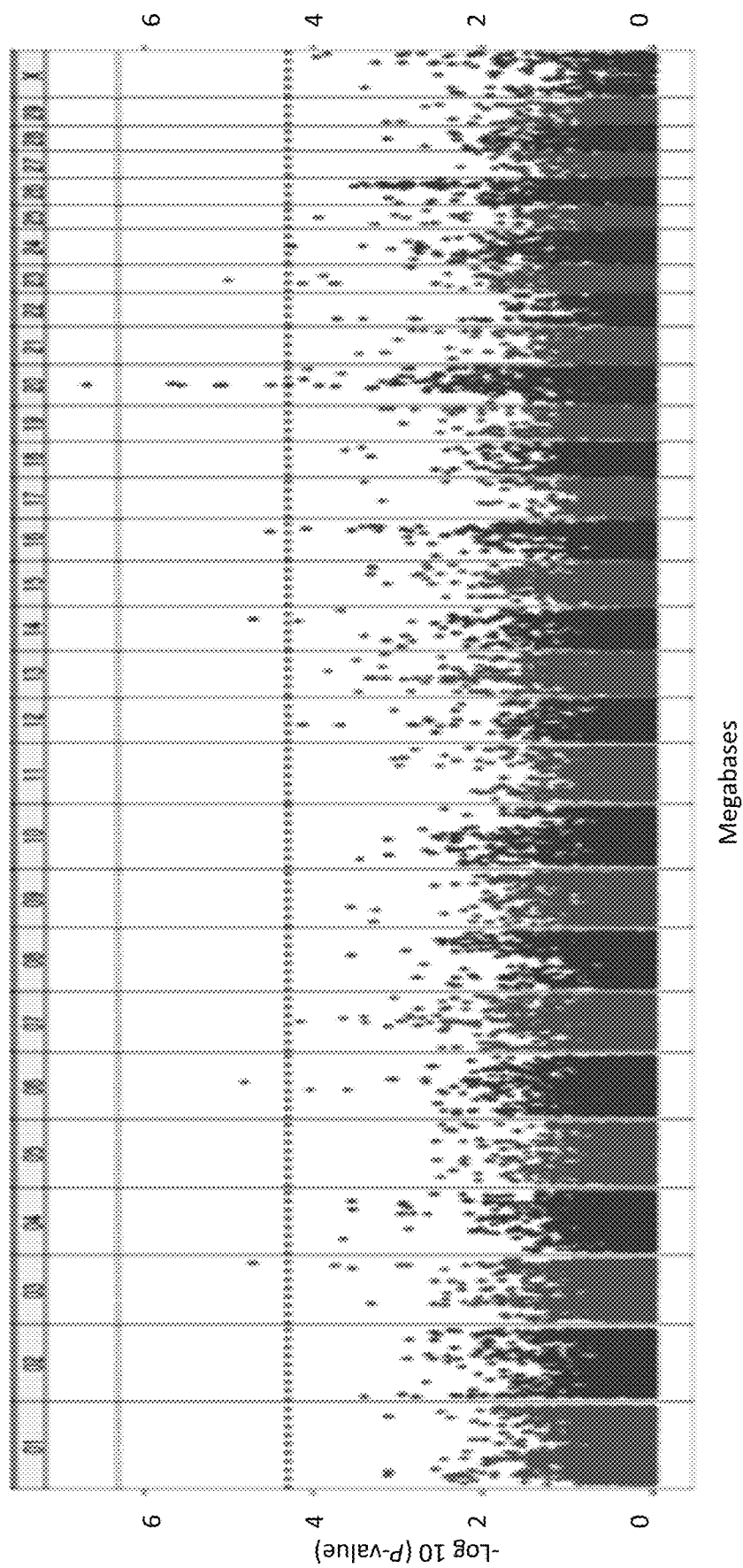
FIG. 3: Results of whole genome scan for genetic marker association with susceptibility to infection of cattle by MAP combining information across populations. Vertical panels denote individual chromosomes as indicated at the top of each panel. Each point represents the –log 10 of the P-value (y-axis) from a linkage disequilibrium analysis (allelic association: top panel, "AS") or a combined linkage-linkage disequilibrium analysis (bottom panel, "LL"), relative to genomic location of the SNP marker (x-axis). A total of 35,772 polymorphic SNP markers were included in the analysis.

The combined analysis of Populations 1 and 2 for individual marker association identified significant results ($P<1\times10^{-7}$) on BTA1, 2, 6, 7, 9, 15, 21 and 24 (FIG. 3). Combining this information with linkage analysis results from Population 1 added BTA5, 20, 22 and 29 to the list.

A total of 1,356 of the most significant markers from the separate and combined analyses were considered in a stepwise logistic regression analysis to identify a subset of markers that could together be used in predicting genomic merit for susceptibility to MAP infection. The cross-validation analysis identified 30 SNPs that appeared in more than half of the models developed with the various subsets of the data (Table 1, FIG. 4). SNPs from seventeen different chromosomes were included, with two or more SNPs included from BTA2, 3, 4, 7, 9, 13, 15, 20, 21, 22 and 29. In one case (BTA21) pairs of SNPs on a common chromosome were in relatively close proximity (<1 Mb), while the remainder were most often in distinct locations (i.e. separated by >20 Mb). A model incorporating the 30 SNPs identified through the cross-validation model development procedure was used on the full data set for purposes of estimating model coefficients (Tables A and B). Based on the concordance of observed and predicted values in the cross-validation testing sets (Table C), a concordance of approximately 72% could be expected.

We claim:

1. A method of prophylactically treating paratuberculosis in a population of cattle, comprising the steps of:
   1) genotyping a biological sample obtained from one or more members of the cattle population, and detecting a genotype selected from the group consisting of:
      (a) SNP BTA-72108-no-rs T/C, wherein one copy of BTA4 comprises SEQ ID NO: 149, and the other copy of BTA4 comprises SEQ ID NO: 149 wherein the 61st nucleotide base is T;
      (b) SNP BTA-116871-no-rs T/C, wherein one copy of BTA17 comprises SEQ ID NO:32, and the other copy of BTA17 comprises SEQ ID NO:32 wherein the 61st nucleotide base is T;
      (c) SNP ARS-BFGL-NGS-41833 T/G, wherein one copy of BTA20 comprises SEQ ID NO:76, and the other copy of BTA20 comprises SEQ ID NO:76 wherein the 61st nucleotide base is T;
      (d) SNP ARS-BFGL-NGS-75935 T/C, wherein one copy of BTA21 comprises SEQ ID NO: 173, and the other copy of BTA21 comprises SEQ ID NO: 173 wherein the 61st nucleotide base is T;
(e) SNP BTA-28297-no-rs G/G, wherein both copies of BTA10 comprise SEQ ID NO:86;
(f) SNP BTA-60642-no-rs A/A, wherein both copies of BTA25 comprise SEQ ID NO:89 wherein the 61st nucleotide base is A;
(g) SNP UA-IFASA-8974 A/A, wherein both copies of BTA20 comprise SEQ ID NO:53 wherein the 61st nucleotide base is A;
(h) SNP BTB-01112664 T/T, wherein both copies of BTA2 comprise SEQ ID NO: 141 wherein the 61st nucleotide base is T;
(i) SNP BTB-00261837 T/T, wherein both copies of BTA6 comprise SEQ ID NO: 14 wherein the 61st nucleotide base is T;
(j) SNP BTA-116871-no-rs T/T, wherein both copies of BTA17 comprise SEQ ID NO:32 wherein the 61st nucleotide base is T;
(k) SNP Hapmap54042-ss46526396 A/A, wherein both copies of BTA22 comprise SEQ ID NO: 13 wherein the 61st nucleotide base is A;
(l) SNP ARS-BFGL-NGS-115504 A/A, wherein both copies of BTA25 comprise SEQ ID NO:60 wherein the 61st nucleotide base is A;
(m) SNP ARS-BFGL-NGS-109845 T/T, wherein both copies of BTA29 comprise SEQ ID NO: 164 wherein the 61st nucleotide base is T;
(n) SNP Hapmap26742-BTA-156593 A/A, wherein both copies of BTA17 comprise SEQ ID NO: 176 wherein the 61st nucleotide base is A; or
(o) SNP ARS-BFGL-NGS-103845 T/C, wherein one copy of BTA7 comprises SEQ ID NO: 146, and the other copy of BTA7 comprises SEQ ID NO:146 wherein the 61st nucleotide base is T; and
2) either:
(a) selectively breeding together two or more members of the cattle population that were genotyped in step 1) as SNP BTA-72108-no-rs T/C, SNP BTA-116871-no-rs T/C, SNP ARS-BFGL-NGS-41833 T/G, SNP ARS-BFGL-NGS-75935 T/C, SNP BTA-28297-no-rs G/G, or SNP BTA-60642-no-rs A/A; or
(b) screening for the presence of *Mycobacterium avium*, ssp. *paratuberculosis* (MAP) or physically separating from the cattle population any of the one or more members of the cattle population that were genotyped in step 1) as SNP UA-IFASA-8974 A/A, SNP BTB-01112664 T/T, SNP BTB-00261837 T/T, SNP BTA-116871-no-rs T/T, SNP Hapmap54042-ss46526396 A/A, SNP ARS-BFGL-NGS-115504 A/A, SNP ARS-BFGL-NGS-109845 T/T, SNP Hapmap26742-BTA-156593 A/A, or SNP ARS-BFGL-NGS-103845 T/C;
whereby paratuberculosis in the cattle population is prophylactically treated.

2. The method of claim 1, wherein in step 2)(b), any of the one or more members of the cattle population that were genotyped in step 1) as SNP UA-IFASA-8974 A/A, SNP BTB-01112664 T/T, SNP BTB-00261837 T/T, SNP BTA-116871-no-rs T/T, SNP Hapmap54042-ss46526396 A/A, SNP ARS-BFGL-NGS-115504 A/A, SNP ARS-BFGL-NGS-109845 T/T, SNP Hapmap26742-BTA-156593 A/A, or SNP ARS-BFGL-NGS-103845 T/C are screened for the presence of MAP.

3. The method of claim 2, further comprising the step of physically separating from the cattle population any of the one or more members of the cattle population that were genotyped in step 1) as SNP UA-IFASA-8974 A/A, SNP BTB-01112664 T/T, SNP BTB-00261837 T/T, SNP BTA-116871-no-rs T/T, SNP Hapmap54042-ss46526396 A/A, SNP ARS-BFGL-NGS-115504 A/A, SNP ARS-BFGL-NGS-109845 T/T, SNP Hapmap26742-BTA-156593 A/A, or SNP ARS-BFGL-NGS-103845 T/C and found through the screening of step 2)(b) to be positive for the presence of MAP.

4. The method of claim 1, wherein in step 2)(b), any of the one or more members of the cattle population that were genotyped in step 1) as SNP UA-IFASA-8974 A/A, SNP BTB-01112664 T/T, SNP BTB-00261837 T/T, SNP BTA-116871-no-rs T/T, SNP Hapmap54042-ss46526396 A/A, SNP ARS-BFGL-NGS-115504 A/A, SNP ARS-BFGL-NGS-109845 T/T, SNP Hapmap26742-BTA-156593 A/A, or SNP ARS-BFGL-NGS-103845 T/C are physically separated from the cattle population.

5. The method of claim 4, wherein before the one or more members of the cattle population that were genotyped in step 1) as SNP UA-IFASA-8974 A/A, SNP BTB-01112664 T/T, SNP BTB-00261837 T/T, SNP BTA-116871-no-rs T/T, SNP Hapmap54042-ss46526396 A/A, SNP ARS-BFGL-NGS-115504 A/A, SNP ARS-BFGL-NGS-109845 T/T, SNP Hapmap26742-BTA-156593 A/A, or SNP ARS-BFGL-NGS-103845 T/C are physically separated from the cattle population, these one or more members of the cattle population are screened for the presence of *Mycobacterium avium*, ssp. *paratuberculosis* (MAP).

6. The method of claim 1 wherein step 1 is performed using a bead chip.

7. The method of claim 1 wherein step 1 comprises a field test.

8. The method of claim 1 wherein step 1 comprises using a visual indicator.

9. The method of claim 6 wherein the bead chip is useful for estimating breeding value in cattle.

* * * * *

SEQUENCE LISTING

<160> NUMBER OF SEQ ID NOS: 197

<210> SEQ ID NO 1
<211> LENGTH: 121
<212> TYPE: DNA
<213> ORGANISM: Bos taurus

<400> SEQUENCE: 1

```
agatgatctg gaccaaatga ttctaaagct tacaaggaga tacaagagca cagtctctgg    60
ggtcagactg cttggtccta atcacagctt cctctcttat cggttgtgtt gccttgggca   120
c                                                                    121
```

<210> SEQ ID NO 2
<211> LENGTH: 121
<212> TYPE: DNA
<213> ORGANISM: Bos taurus

<400> SEQUENCE: 2

```
ccacatgctg tgggccaact aagcccaaac acctcagtta ctgagcccac attctagagc    60
ccccatgcca aactaggaa gaaggccaca ctccgcagct agagaagccc gggcgctgcc   120
a                                                                    121
```

<210> SEQ ID NO 3
<211> LENGTH: 121
<212> TYPE: DNA
<213> ORGANISM: Bos taurus

<400> SEQUENCE: 3

```
gggaatggat cagtgacttc acttgggcat catgtaaatg ccagcttttc atgacttact    60
gatgtctgcc agggccaaat taaacttgcc acttcaatga atgaaaacag cccaaacaca   120
a                                                                    121
```

<210> SEQ ID NO 4
<211> LENGTH: 121
<212> TYPE: DNA
<213> ORGANISM: Bos taurus

<400> SEQUENCE: 4

```
gcttctagtt tgctttgtgt gggatggggt cacaggtcac agccagtctt ttatcactta    60
caacaataaa gatggtcttc tttcttaaac tttaaatgca ggaagcttag attgttttct   120
a                                                                    121
```

<210> SEQ ID NO 5
<211> LENGTH: 121
<212> TYPE: DNA
<213> ORGANISM: Bos taurus

<400> SEQUENCE: 5

```
cccctgctcc aaaggccagg ttctctccat aggaagtgcc cagtactgac tgcgtggggc    60
cacagagaaa gagcctcttt cttgttagtt gttattgttg tagttgttat cttatcgtag   120
c                                                                    121
```

<210> SEQ ID NO 6
<211> LENGTH: 121
<212> TYPE: DNA
<213> ORGANISM: Bos taurus

<400> SEQUENCE: 6

```
aagtctttat tgaatttgtt agaatgttgc ttccgggttt tttgttttgc tttggttttc    60
cggccttgag gcatgtagga tcttagcccc ctgaccagag atcaaactta tatcctctgc   120
a                                                                    121
```

<210> SEQ ID NO 7
<211> LENGTH: 121
<212> TYPE: DNA
<213> ORGANISM: Bos taurus

<400> SEQUENCE: 7
aatactagaa gctgcagagc tatcaccgtg aactgacaca gatcctgccc tttccaaact      60
gaagaggtta acaggtgatt tatgatgtgt gcataataat taactgtgca aggtagaaaa     120
t                                                                     121

<210> SEQ ID NO 8
<211> LENGTH: 121
<212> TYPE: DNA
<213> ORGANISM: Bos taurus

<400> SEQUENCE: 8
caaggtttca ccttctgaaa catttttccct taatgtagga atagtatctc caggaatacc     60
ggtgtctggt gttatttata atatgaggac cctgagacag tgtgtccatt tccagaaatt    120
c                                                                     121

<210> SEQ ID NO 9
<211> LENGTH: 121
<212> TYPE: DNA
<213> ORGANISM: Bos taurus

<400> SEQUENCE: 9
gcaggcaatt tacttctatt ggcatttctt gggtagtttc ccaacgttca ggccaagcga      60
cttaactgag agcacagcca cattctcaac tgtgagtttc catttctgtg agttgcccag    120
a                                                                     121

<210> SEQ ID NO 10
<211> LENGTH: 121
<212> TYPE: DNA
<213> ORGANISM: Bos taurus

<400> SEQUENCE: 10
caccgtggcc actgacccca tcgagaggct tcgcctgcag tgcctggcca ggggctcagc      60
gggcatcaaa gggcttggca ggtaggacct gggctgtggg ctgcagggag atgaaggaga    120
a                                                                     121

<210> SEQ ID NO 11
<211> LENGTH: 121
<212> TYPE: DNA
<213> ORGANISM: Bos taurus

<400> SEQUENCE: 11
aggaatacac acagttacat gtggtccaga gagtcgtaca aagtagccac tgcagggcca      60
cgctgctgat tgctgaccac ttgcccctct gctggcactc ctacatattg tttgccgaac    120
a                                                                     121

<210> SEQ ID NO 12
<211> LENGTH: 121
<212> TYPE: DNA
<213> ORGANISM: Bos taurus

<400> SEQUENCE: 12
tgaccttgag taatgaggct cttcagctgc ggcaattttg aggtgggctg atagccgagc      60

```
gctgcctgcc tgcagcccgc tcaacagctg agaatagaaa tccttcagac ttgaaaggga    120
a                                                                   121

<210> SEQ ID NO 13
<211> LENGTH: 121
<212> TYPE: DNA
<213> ORGANISM: Bos taurus

<400> SEQUENCE: 13
cataaaagct gcctccggcc tggccttcta gcctcagccc agtcaaaagt cccaccttta    60
ccatttgatt tggtgtgtgc ccttagaggg aattcagagc tccgttaggc tcatagaggg    120
g                                                                   121

<210> SEQ ID NO 14
<211> LENGTH: 121
<212> TYPE: DNA
<213> ORGANISM: Bos taurus

<400> SEQUENCE: 14
aaaacttctt gtttcctggt tatgcatcct catcttattc tttttatagt catagtagta    60
ctttttcccc atttactacc attttaaaga ttatatgaaa tgacaatgta actgttgttt    120
a                                                                   121

<210> SEQ ID NO 15
<211> LENGTH: 121
<212> TYPE: DNA
<213> ORGANISM: Bos taurus

<400> SEQUENCE: 15
aaagtgtggc tggggacaca tcagaatgca tatggcgggc agatcagaca gtgtggcctc    60
gagcacatga taaaaagaca ttgtctgtaa tggatattga agtccctagc ctgacctcca    120
g                                                                   121

<210> SEQ ID NO 16
<211> LENGTH: 121
<212> TYPE: DNA
<213> ORGANISM: Bos taurus

<400> SEQUENCE: 16
gacagaaaaa agaatataag gggtgccagg aggcaaaaag gcggggcccc aggaccacag    60
cgttccctgc cagcagcccc cttcaccctc cttccactca tctgccccag tcctaaaggt    120
c                                                                   121

<210> SEQ ID NO 17
<211> LENGTH: 121
<212> TYPE: DNA
<213> ORGANISM: Bos taurus

<400> SEQUENCE: 17
caggttgtgg ggaggataat aataaccata ggtcttgggc caggcttgtg taagtgctct    60
gtgtgtattg tctccctaag agtcctcaca ggtgctagtt ttgcttgca ggctgagttg    120 c                                                                   121

<210> SEQ ID NO 18
<211> LENGTH: 121
<212> TYPE: DNA
```

<213> ORGANISM: Bos taurus

<400> SEQUENCE: 18

| gagctgtgca gaacagaagc ttttataag ctgtagggcg gggcaaggaa gtcatagcaa | 60 |
| gaggaaagaa agggttattt ggggccagga catcgttttt tgggcaaaag gactggttta | 120 |
| a | 121 |

<210> SEQ ID NO 19
<211> LENGTH: 121
<212> TYPE: DNA
<213> ORGANISM: Bos taurus

<400> SEQUENCE: 19

| cttgacatca ttcatcatgg atgggatgtc tttgactgca aaatggaaac tcaaagtagt | 60 |
| gtttcctggc ccctggggag ggggctgttg ggggaggatg ggggctgggt tcggagcccc | 120 |
| a | 121 |

<210> SEQ ID NO 20
<211> LENGTH: 121
<212> TYPE: DNA
<213> ORGANISM: Bos taurus

<400> SEQUENCE: 20

| aaaaattaaa ttaaaatatt ttgtgggccc ctgaaagtat tgcaggcctt tggcactgtg | 60 |
| cctcctgtgg atacgactca agccacttag cagcagcagc agctcctgtg gataagctgg | 120 |
| c | 121 |

<210> SEQ ID NO 21
<211> LENGTH: 121
<212> TYPE: DNA
<213> ORGANISM: Bos taurus

<400> SEQUENCE: 21

| agcacataaa actagaacat ggtctctgca cactggttct aagtcagtgt gacagatgac | 60 |
| gcatgtgtgt gctcactcag tcatgtccgg cccttgggga ccccatggac tggagcccac | 120 |
| c | 121 |

<210> SEQ ID NO 22
<211> LENGTH: 121
<212> TYPE: DNA
<213> ORGANISM: Bos taurus

<400> SEQUENCE: 22

| aggcttcaat cctgcagaga ctgtgagtct gtgagtctga ctggggcccg gggttctacg | 60 |
| ctgctcacaa gcccccaggt gatcccccac tgccggacca cccttctcca agtatgtacc | 120 |
| a | 121 |

<210> SEQ ID NO 23
<211> LENGTH: 121
<212> TYPE: DNA
<213> ORGANISM: Bos taurus

<400> SEQUENCE: 23

| tcctctgtgt tgtacagcag aaactgacag agcattttaa aacagttaca ttccaataaa | 60 |
| gaagaagaaa aatgtctggc cccatttttt ttgtggcatg aaactttggc tttagttttc | 120 |
| a | 121 |

<210> SEQ ID NO 24
<211> LENGTH: 121
<212> TYPE: DNA
<213> ORGANISM: Bos taurus

<400> SEQUENCE: 24

```
aggggggcagg ggggagggtt tgatggcaca atttgctgtc ccttcctcaa gtgcatgggc    60
gacttcagga tgttcgtgat gaattttaag tttccccgag acagtcagt tctggagaaa    120
t                                                                    121
```

<210> SEQ ID NO 25
<211> LENGTH: 121
<212> TYPE: DNA
<213> ORGANISM: Bos taurus

<400> SEQUENCE: 25

```
atattataaa tattcatcca agccttcctt gaagggatct gtagacattt acaaatttaa    60
cgagagttat taggtactga ctcggtactg aagcaagccc cctgagaccc aaacactact    120
g                                                                    121
```

<210> SEQ ID NO 26
<211> LENGTH: 121
<212> TYPE: DNA
<213> ORGANISM: Bos taurus

<400> SEQUENCE: 26

```
caccaatgtg cttgttcttg agtctgctga gactgggtct ggagctggaa tatgggtggg    60
gatggaggga aagtgtccgg tggggcaacg ttcatagact tacacgattc ctcagcagga    120
c                                                                    121
```

<210> SEQ ID NO 27
<211> LENGTH: 121
<212> TYPE: DNA
<213> ORGANISM: Bos taurus

<400> SEQUENCE: 27

```
aaggttttct tgagtctttt ctgagccttt tcctgagcat gtgaaattac tttctaattt    60
cctccatata ttagttgttt taaatgttct aatgtctagc tcccagagtc tttattggta    120
t                                                                    121
```

<210> SEQ ID NO 28
<211> LENGTH: 121
<212> TYPE: DNA
<213> ORGANISM: Bos taurus

<400> SEQUENCE: 28

```
tagtggtata gatctgtggg tagcgtcgac gcagagcaca taaagcagct tcagagcata    60
ctgacttgat atctgcacca cagtatccta tccaaggcaa ccaaaaaaga aaaaaatta    120
a                                                                    121
```

<210> SEQ ID NO 29
<211> LENGTH: 121
<212> TYPE: DNA
<213> ORGANISM: Bos taurus

<400> SEQUENCE: 29

```
aggtgctatt atgcaggtac tacttttgaa aacttttttcc ttctgattgt cttttcctaa    60
cctgttccct tttgtctcct ctctcgtaga atattattga ttcctaatga ttttaccatc   120
c                                                                   121

<210> SEQ ID NO 30
<211> LENGTH: 121
<212> TYPE: DNA
<213> ORGANISM: Bos taurus

<400> SEQUENCE: 30
catatcttaa ggaattttt tgtgacctgt agtaatcctg aaatatttga gattggacct    60
catccaattt ctggatcaat aaggtacaga gtacctgtat tatgctgaag atatatgaga   120
a                                                                   121

<210> SEQ ID NO 31
<211> LENGTH: 121
<212> TYPE: DNA
<213> ORGANISM: Bos taurus

<400> SEQUENCE: 31
ggggtggagg gacatcccag ggaccctgc tgacctctct gaaacttggt cagaacatcg    60
gagttaggaa tccattaaag gccgcctcga ggaacctgcg acttccctcc aaggaggagc   120
a                                                                   121

<210> SEQ ID NO 32
<211> LENGTH: 121
<212> TYPE: DNA
<213> ORGANISM: Bos taurus

<400> SEQUENCE: 32
aattactctt ccattctgtc ctgatggcgc aggccatgga tttccttagg tctgctccty    60
cggagctgta acattcactt tcatttcttt caaaagtttt tcttactctc acttttcaat   120
a                                                                   121

<210> SEQ ID NO 33
<211> LENGTH: 121
<212> TYPE: DNA
<213> ORGANISM: Bos taurus

<400> SEQUENCE: 33
caccgccacc aaaaaaaaga tacatggggt gaggagatga atttaataga aggttttaaa    60
tttacatctt aaatatagaa gggcatgtgc acatgtgctc agtcgtttca gtcgtgtccg   120
a                                                                   121

<210> SEQ ID NO 34
<211> LENGTH: 121
<212> TYPE: DNA
<213> ORGANISM: Bos taurus

<400> SEQUENCE: 34
tcaacagtaa tgtattgtac acttaacatt tgttaaatga aggtatattt tatgctgttt    60
cttatcataa taaaattaaa ttaaaaagta cacacatgtg cacacacata catacaaaaa   120
a                                                                   121

<210> SEQ ID NO 35
<211> LENGTH: 121
```

```
<212> TYPE: DNA
<213> ORGANISM: Bos taurus

<400> SEQUENCE: 35
gggcccctcc taagtctcag tgccccacag ggcccatgtg gctgcccact ccttctcgtc      60
ctcagctagc agaccccgaa agcagggtga ggcccattag ccttggctat cacccggtca     120
a                                                                     121

<210> SEQ ID NO 36
<211> LENGTH: 121
<212> TYPE: DNA
<213> ORGANISM: Bos taurus

<400> SEQUENCE: 36
tagaatcaga atctaaaaat catcactaga atcactgaaa ccaaaggagt gtatagtagt      60
gggtataatt ctaccaatga tattgtaagt tagtgttatc tcattaggta taccaggaaa    120
a                                                                     121

<210> SEQ ID NO 37
<211> LENGTH: 121
<212> TYPE: DNA
<213> ORGANISM: Bos taurus

<400> SEQUENCE: 37
aaggctggaa aaaaattttt ttttaatcta tctccctcaa aaaagcaagc aaacaagaca      60
cagcaacatt gttttctaga aaatggcag tattacactg aaaatcaaga acaacccaag     120
a                                                                     121

<210> SEQ ID NO 38
<211> LENGTH: 121
<212> TYPE: DNA
<213> ORGANISM: Bos taurus

<400> SEQUENCE: 38
acagtcaaca agttgtgtgc tgtttgttcc tggcccattg acaccacgtc aaggcttgag      60
caaaaaagaa ttaaactctt caacccaaat ctcctcttca ttctgtcagg gccacccaaa    120
g                                                                     121

<210> SEQ ID NO 39
<211> LENGTH: 121
<212> TYPE: DNA
<213> ORGANISM: Bos taurus

<400> SEQUENCE: 39
catgttctca tctggaagac agaagttcta tcatgagtcc tgcacatacc cctggatgat      60
cggactaggg atatgagagt gccttgaaaa caatgaaatg ctatttaagt gagagctacc    120
a                                                                     121

<210> SEQ ID NO 40
<211> LENGTH: 121
<212> TYPE: DNA
<213> ORGANISM: Bos taurus

<400> SEQUENCE: 40
attttgttta aactgtttct tttggctgtc aacctttgat ggccttcttt gctatgcaaa      60
gaaatgttca ataagacctg attgtaacca atagcacaga atcattaatt tccgccttag    120
``` c 121

<210> SEQ ID NO 41
<211> LENGTH: 121
<212> TYPE: DNA
<213> ORGANISM: Bos taurus

<400> SEQUENCE: 41
gacctcagct tatggtacag agggtgcaag acggatctct cgtcacggaa ctaagatccc    60
gtgtgacttg tggccaagga agccaaaaca taaagcagga acaatatcgt gacaaattca   120
a                                                                   121

<210> SEQ ID NO 42
<211> LENGTH: 121
<212> TYPE: DNA
<213> ORGANISM: Bos taurus

<400> SEQUENCE: 42
actagacttg tcatcagttt gtagtgtata caaataataa ataatgctgt atacctgaaa    60
cttggaagga aagttatgac caacctagat agcatattca aaagcagaga cattactttg   120
c                                                                   121

<210> SEQ ID NO 43
<211> LENGTH: 121
<212> TYPE: DNA
<213> ORGANISM: Bos taurus

<400> SEQUENCE: 43
ccgaaatgaa acttcttaag gatgaaataa aattattatt agcagatggt tattttaatc    60
gtcttcaaag cttttgggga gtctagcatt gtcaggcaga tgcagtggca tcacacacat   120
a                                                                   121

<210> SEQ ID NO 44
<211> LENGTH: 121
<212> TYPE: DNA
<213> ORGANISM: Bos taurus

<400> SEQUENCE: 44
ccataggctg tgctttgttc ccagagctca cctaacagcc cacacaaatg agtaattatc    60
cgtggccagc atggtcttta caaagaagag acaggggtgc cttaggccag gtgaggtaag   120
g                                                                   121

<210> SEQ ID NO 45
<211> LENGTH: 121
<212> TYPE: DNA
<213> ORGANISM: Bos taurus

<400> SEQUENCE: 45
gcctgaggaa ttgaggggct gtcgctgcgc cccagctgct cttccagacg ctgacgggac    60
ggaggagtga aatgccgcct ttccttcctc tgccctcccc cccagacggc gtcagaaccg   120
c                                                                   121

<210> SEQ ID NO 46
<211> LENGTH: 121
<212> TYPE: DNA
<213> ORGANISM: Bos taurus

<400> SEQUENCE: 46

```
atgtgggttc gcggtgggcg aggaggggca gcgctgcgct tggccgagtg cctgcttgtt    60
gctcccccaa acctcacagg cagactcaca ggcaaacgtc tccttgagtt tcctgtgtga   120
c                                                                  121
```

<210> SEQ ID NO 47
<211> LENGTH: 121
<212> TYPE: DNA
<213> ORGANISM: Bos taurus

<400> SEQUENCE: 47

```
tgcttaattt cacaccaaaa ggagagcgct ttgggtgtga gggagggccc aaggggggcaa    60 cgcccccaaa aagaaagatg aaggatgtcc ttacatgaaa acgagtgaag ccaacatccc   120
a                                                                  121
```

<210> SEQ ID NO 48
<211> LENGTH: 121
<212> TYPE: DNA
<213> ORGANISM: Bos taurus

<400> SEQUENCE: 48

```
ctctagatca tcatgaggtt ccaattctag ttcagagtgt aagtaaagtt atggttataa    60
cctctgtcac agaaaaaata aatatatctt ggcaacacat tagtagtttt gctgatgaga   120
a                                                                  121
```

<210> SEQ ID NO 49
<211> LENGTH: 121
<212> TYPE: DNA
<213> ORGANISM: Bos taurus

<400> SEQUENCE: 49

```
ggtctgtgga gttgtgggtg tcagagtgga aacaaatcca gggcacattc tcaggattgg    60
ctgacagagg tgggatggag ctgagggaca tggagtgagg ggtcaagaga gaggccaggg   120
a                                                                  121
```

<210> SEQ ID NO 50
<211> LENGTH: 121
<212> TYPE: DNA
<213> ORGANISM: Bos taurus

<400> SEQUENCE: 50

```
gccagaagcc acccatgaat acagaggatc cccaggaaga tgagagcccc accaagactg    60
cggctccaca gagagggccc ctggtccccc tggcagccaa ggccaagtct ggcccttga    120 a                                                                  121
```

<210> SEQ ID NO 51
<211> LENGTH: 121
<212> TYPE: DNA
<213> ORGANISM: Bos taurus

<400> SEQUENCE: 51

```
acatgaaggt gaaggcattt ggttcttcta agaatggcaa cagcaatgac aattttagat    60
gtatcaagtt ctgatgaggg ccgaggtaac caggttctgg gactcactgt ggcagcctct   120
c                                                                  121
```

<210> SEQ ID NO 52

```
<211> LENGTH: 121
<212> TYPE: DNA
<213> ORGANISM: Bos taurus

<400> SEQUENCE: 52 cccctttct ggagctgctt gtcccttga tggatagttc aggcctgtgg tgtggatagc    60
gccttctgca tggctcctgc tgctgctttg aagacatttc actgtctgtg gttccctaac   120
c                                                                   121

<210> SEQ ID NO 53
<211> LENGTH: 121
<212> TYPE: DNA
<213> ORGANISM: Bos taurus

<400> SEQUENCE: 53
aactgggggt agaatcagca tcttaatcct tgaaaacaaa attttgtttt gatgtaagtt    60
cctcattctc atttcaaaag acagaaataa aatattgaca atattattac taatataaag   120
t                                                                   121

<210> SEQ ID NO 54
<211> LENGTH: 121
<212> TYPE: DNA
<213> ORGANISM: Bos taurus

<400> SEQUENCE: 54
gagtggttga taagctctgt tcctgtgtgt aatgaaggta gaagaaatag ctattcacca    60
ctattaattt aagcattgag cacttgatat cagagtttga ctataagtaa tacatcatgg   120
a                                                                   121

<210> SEQ ID NO 55
<211> LENGTH: 121
<212> TYPE: DNA
<213> ORGANISM: Bos taurus

<400> SEQUENCE: 55
gatggtttcc atttgtaatt attactgaaa agcatgtggt cttgtgggcc ctctcatagc    60
cgttcacaag ggggtggacc tgtgaagagg tctggacagt gtacctggtt ttaaaccagg   120
c                                                                   121

<210> SEQ ID NO 56
<211> LENGTH: 121
<212> TYPE: DNA
<213> ORGANISM: Bos taurus

<400> SEQUENCE: 56
aaatattaca ttatgtatag tacttgaact atgcatatga tattctaaga ttttttaaatc   60 caagtgtagt catttaacat ttgtggaagt ggtttcattc tttgatacgt agtaatgcat   120
g                                                                   121

<210> SEQ ID NO 57
<211> LENGTH: 121
<212> TYPE: DNA
<213> ORGANISM: Bos taurus

<400> SEQUENCE: 57
gatgtgaagg tgaatgccat cagggtcagg tgtgaatgag gttgcggcct gccctccatc    60
cgccgttgct gacgatcctt cagctctaca cctcccacct cctgttggaa acccttgcag   120
``` a                                                                         121

<210> SEQ ID NO 58
<211> LENGTH: 121
<212> TYPE: DNA
<213> ORGANISM: Bos taurus

<400> SEQUENCE: 58
agagtaaaat acttaggagt taagtgtgtg cctggcttgg atcttaacca tccttggact      60
gtctgggctt tgtgctagtc acgcttctgc ttgtctgtgt tctgctgcct gatcagctgt     120
g                                                                         121

<210> SEQ ID NO 59
<211> LENGTH: 121
<212> TYPE: DNA
<213> ORGANISM: Bos taurus

<400> SEQUENCE: 59
agttaactgc ccactttttt taaaaaaaaa tcagtttctt cagaggaaca caacaaaatc      60
cgggggctct acaatatata tcattcatga atggatacta cgcaaaatac taagtacatg    120
a                                                                         121

<210> SEQ ID NO 60
<211> LENGTH: 121
<212> TYPE: DNA
<213> ORGANISM: Bos taurus

<400> SEQUENCE: 60
ctaactttca gcggcccact ggaatctctg cttggagccc acggccatct cacactgagc      60
gtttctttct tgctcctctt gggttttttc tgtggagtat cactgtcctc cttctcaccc    120
a                                                                         121

<210> SEQ ID NO 61
<211> LENGTH: 121
<212> TYPE: DNA
<213> ORGANISM: Bos taurus

<400> SEQUENCE: 61
agaagaactg ctatcagttc cccaccatca aacaccattc cgtttctatg gattacgggc      60
caaggtccat cttctgtaac ttcgtcttga cacagtgtgc tgtattctca gagtggaaga    120
t                                                                         121

<210> SEQ ID NO 62
<211> LENGTH: 121
<212> TYPE: DNA
<213> ORGANISM: Bos taurus

<400> SEQUENCE: 62
aatgaagaag ccttcgaagt gctagtggga agctgctgta taacacaggg agctcagctc      60
ggtgtcttgt aatggcctag aggggtgaag aatcagcctg caatgtggga gacccagatt    120
c                                                                         121

<210> SEQ ID NO 63
<211> LENGTH: 121
<212> TYPE: DNA
<213> ORGANISM: Bos taurus

<400> SEQUENCE: 63
ctatgatttc atggtgaaat acttgggatc tcccaccaca tctgtctcca tactggttgc        60
cctagataag aacttggtaa tttgagttga tttaacaagg taatttgatt gttatttaaa       120
a                                                                      121

<210> SEQ ID NO 64
<211> LENGTH: 121
<212> TYPE: DNA
<213> ORGANISM: Bos taurus

<400> SEQUENCE: 64
actgagggac tatgagaaaa gtagtagact aggggctgaa ggaaagataa agaaatcaga        60
ggagagtcta aggaacttca ctgacagcag agcatcagta aagcaaggag agaatagaag       120
a                                                                      121

<210> SEQ ID NO 65
<211> LENGTH: 121
<212> TYPE: DNA
<213> ORGANISM: Bos taurus

<400> SEQUENCE: 65
agggcactga aaaccaagag aggaccacag atgatgctgg ccatctctga cacctccact        60
cacacagtcg ttttccactt catttcaaac aaacaggagc tggagggagg ggtatggtag       120
g                                                                      121

<210> SEQ ID NO 66
<211> LENGTH: 121
<212> TYPE: DNA
<213> ORGANISM: Bos taurus

<400> SEQUENCE: 66
ccacttgtat gagcctatga cataggccac ctcactgatt ttagggatca gtcaaaagga        60
cttkatgtcc cacccagttc tctataaaat aagcaaagtg agcctcctac tcattttctg       120
a                                                                      121

<210> SEQ ID NO 67
<211> LENGTH: 121
<212> TYPE: DNA
<213> ORGANISM: Bos taurus

<400> SEQUENCE: 67
cctagccggc aacaggacta ttgagctccc tatgaccttt cttcctgcaa acggccccg        60 cgggagaagt cgaggctgga ccccagaaag gacttccttt gattaaaatg tggcaatgac       120
g                                                                      121

<210> SEQ ID NO 68
<211> LENGTH: 121
<212> TYPE: DNA
<213> ORGANISM: Bos taurus

<400> SEQUENCE: 68
agatcagtta actatactta caagggttta ttttagtatt ttctgttctg ttgttttgtt        60
gttgtttatt tgctaagtcg tgttggcctc ttttgcaacc ccatggagtg tggagccacc       120
a                                                                      121

```
<210> SEQ ID NO 69
<211> LENGTH: 121
<212> TYPE: DNA
<213> ORGANISM: Bos taurus

<400> SEQUENCE: 69
ggtctctgag cccagaaccc cgctctctgt tcctgtagcc cattggagat ggttccagtt      60
ggggcccttc agagttctca gatgttgaat ggattcaagt cctggtgttg attggtttgc     120
a                                                                    121

<210> SEQ ID NO 70
<211> LENGTH: 121
<212> TYPE: DNA
<213> ORGANISM: Bos taurus

<400> SEQUENCE: 70 actcttttg tttttcagc aaacattgtt cactacttac ttggcccctg acaaccttaa      60
cgcatctgaa atggaacact ccctatgtgc atggccatgt ccaatcactg agcaagagag     120
g                                                                    121

<210> SEQ ID NO 71
<211> LENGTH: 121
<212> TYPE: DNA
<213> ORGANISM: Bos taurus

<400> SEQUENCE: 71
acacaatagg tgctcagtat atatatttat ggaacacacg tggataggaa caaaggggcc      60
cactcactct ggagctaggt ttctccgggc ttcaacttgg caattcccag tgcccacaga     120
g                                                                    121

<210> SEQ ID NO 72
<211> LENGTH: 121
<212> TYPE: DNA
<213> ORGANISM: Bos taurus

<400> SEQUENCE: 72
cgcccacggc atctctctgt ctttgtcact gccttgcctt ctttattctc taacttggct      60
cccctagtca cacattaagg aaggctttcc ctggtggcgc tgtggataag aatccggcga     120
c                                                                    121

<210> SEQ ID NO 73
<211> LENGTH: 121
<212> TYPE: DNA
<213> ORGANISM: Bos taurus

<400> SEQUENCE: 73
ctcctgcatt gcaggcagat gttttaccct ctaagccaga gtaaactctt caataatagc      60
cttatattgg tccatatact ctcatttgtg gcattttaaa attctgttca ctccttcccc     120
a                                                                    121

<210> SEQ ID NO 74
<211> LENGTH: 121
<212> TYPE: DNA
<213> ORGANISM: Bos taurus

<400> SEQUENCE: 74
atcgaccctg agataagaat ccctgcctta gatgcttgcc atatttgaaa agaaagctaa      60
```

```
ggttttatca tttcacagca gtcttagtac cctggagagc ctctgtattt taagttgctc    120
a                                                                    121

<210> SEQ ID NO 75
<211> LENGTH: 121
<212> TYPE: DNA
<213> ORGANISM: Bos taurus

<400> SEQUENCE: 75
agctgatcct actgaggcag cctgggttca gtcctcccag ccctggcccc cagtttccgg    60
cgcagctgtt cccgagatac ctgagcaaag ccctgagcga tcctgggcgc gtggcaggca    120
a                                                                    121

<210> SEQ ID NO 76
<211> LENGTH: 121
<212> TYPE: DNA
<213> ORGANISM: Bos taurus

<400> SEQUENCE: 76
gagaggagcc ttttcttctg cagtgctgcc cgccccacat cctcttgggt ggagctccac    60
gtccctgttg cagatggcct tctcctcttg tgccttcaaa tggcagaggg tgatagagag    120
a                                                                    121

<210> SEQ ID NO 77
<211> LENGTH: 121
<212> TYPE: DNA
<213> ORGANISM: Bos taurus

<400> SEQUENCE: 77
aataatacaa tgttaataga aatgggccat gtattgagtc gtcatttaaa cataagtaat    60
ctcttggtcc aaattagtga aaccttaaaa aaaaaaagg attgtctcta gagaacatca     120
t                                                                    121

<210> SEQ ID NO 78
<211> LENGTH: 121
<212> TYPE: DNA
<213> ORGANISM: Bos taurus

<400> SEQUENCE: 78
tgacggcaga aggctggggg cctgctttgt gattttcccc cttgggcttg acacatgtta    60
cacacagctt ctgctccccc tgccagtacc tccaatacct gctgcaggga ccctgatgac    120
a                                                                    121

<210> SEQ ID NO 79
<211> LENGTH: 121
<212> TYPE: DNA
<213> ORGANISM: Bos taurus

<400> SEQUENCE: 79
agttagtcta gcatccaact tttatgattc accctaagaa aataattgga aaagtgtgca    60
gagatgattg tgtgagatca ttaaagtatt atttataata gtgaacaaac acaaacaagc    120
a                                                                    121

<210> SEQ ID NO 80
<211> LENGTH: 121
<212> TYPE: DNA
<213> ORGANISM: Bos taurus
```

<400> SEQUENCE: 80
ataataactc tacctcactt tagcacaggt tcctgcacag aagtctggta ccaggaaaac    60
ggcgaaacca gaaaggagca aggccctgaa tagcacccgg gaattgtccc cagtggcctt   120
g                                                                  121

<210> SEQ ID NO 81
<211> LENGTH: 121
<212> TYPE: DNA
<213> ORGANISM: Bos taurus

<400> SEQUENCE: 81
attatctatt tggtttgcaa ttctatttac ttatttatct ttttggccat attgtgtggc    60
ttgcaggatc ttaatccctg accagggatt gaacccgtat gctctgcatt gagagcacag   120
a                                                                  121

<210> SEQ ID NO 82
<211> LENGTH: 121
<212> TYPE: DNA
<213> ORGANISM: Bos taurus

<400> SEQUENCE: 82
ccaggaaact ctgattaaaa aaaaaaacaa acaacctaaa aaactaagaa agcaattaag    60
cttcacttat gtttaacatg ccaagtaaca ggtatatgct atgcattgga aatgcaggct   120
c                                                                  121

<210> SEQ ID NO 83
<211> LENGTH: 121
<212> TYPE: DNA
<213> ORGANISM: Bos taurus

<400> SEQUENCE: 83
tcctaggtag gtgggcccctt gctgacccaa caggcagtga taatcgagga aaggccaagg    60
gtttggctag tatctcccat ccctctgcta gccttcccca gtgtctgtcc tagtttctga   120
a                                                                  121

<210> SEQ ID NO 84
<211> LENGTH: 121
<212> TYPE: DNA
<213> ORGANISM: Bos taurus

<400> SEQUENCE: 84
catttctatg tctgcctctc cccacaaaga gttttcttaa tctactggtc ttcatttaca    60
gtcttatttc cagaacacaa aatcaggcat ggaagatgct cagtaaatgt taggagaact   120
a                                                                  121

<210> SEQ ID NO 85
<211> LENGTH: 121
<212> TYPE: DNA
<213> ORGANISM: Bos taurus

<400> SEQUENCE: 85
cttgaattca aaaatagact gttttgatac ggggaggaca attagctatt aataccagct    60
gaattttctc actcgttcta ataaaggctt tcttcctgtt ataggtttcc accatgaatg   120
a                                                                  121

<210> SEQ ID NO 86
<211> LENGTH: 121
<212> TYPE: DNA
<213> ORGANISM: Bos taurus

<400> SEQUENCE: 86

```
aattaaagtt ccaatgataa tagatttgaa aatataataa ataagaggat agtaatgaaa    60
gtaatattaa gggagtagga gagtatggct acaaatttct tctaaaagga aaagatggat   120
g                                                                   121
```

<210> SEQ ID NO 87
<211> LENGTH: 121
<212> TYPE: DNA
<213> ORGANISM: Bos taurus

<400> SEQUENCE: 87

```
gacaaatttt aagtatacct caagtgttcc tataaattta agacatttag taatacttca    60
gggtggcttg caacttaaat tctataactt ttgttaggaa gtgtaggatt ccattgtgga   120
a                                                                   121
```

<210> SEQ ID NO 88
<211> LENGTH: 121
<212> TYPE: DNA
<213> ORGANISM: Bos taurus

<400> SEQUENCE: 88

```
gagttccagt gtttggggac aaacactgct gtggaaggaa cgtgtgaaaa ggccacagtc    60
ctgtcagtga atgaggaagg ctgtgctttc tgtgtgcttc aagcagggaa gctgtcactc   120
a                                                                   121
```

<210> SEQ ID NO 89
<211> LENGTH: 121
<212> TYPE: DNA
<213> ORGANISM: Bos taurus

<400> SEQUENCE: 89

```
aaatgctttc aggttttcac cattgagaat gaaatttgct gtgggttcgt catatggctt    60
ctattatgtt aaggtagttt ccctctatgc ccactttctg gagagttttt ttatcataca   120
t                                                                   121
```

<210> SEQ ID NO 90
<211> LENGTH: 121
<212> TYPE: DNA
<213> ORGANISM: Bos taurus

<400> SEQUENCE: 90

```
gactgaactc cttccaaaac agacctgttc tgtcactctc tttcatctca ggcaatagca    60
cttctatcct tggggcccctt cctgactact gtctctctcc ccaacccacg accaatccat  120
c                                                                   121
```

<210> SEQ ID NO 91
<211> LENGTH: 121
<212> TYPE: DNA
<213> ORGANISM: Bos taurus

<400> SEQUENCE: 91

```
caacagtatt gtagccagat atccaaacta gtagaacatt ttaacctctt tgacctcttg    60
```

```
gatacctgct ttttttttta aattgaagta tagttgattt acaatatagt gttagtttca    120
a                                                                    121

<210> SEQ ID NO 92
<211> LENGTH: 121
<212> TYPE: DNA
<213> ORGANISM: Bos taurus

<400> SEQUENCE: 92
agaatatcca agagactagt gaaaggccac tgaattatgg gtataccaaa taaatacgat    60
ggcacctaac aaccaaagct gcaatgacat caccccccagg aaaatgctgg ctgtcaaatt   120
c                                                                    121

<210> SEQ ID NO 93
<211> LENGTH: 121
<212> TYPE: DNA
<213> ORGANISM: Bos taurus

<400> SEQUENCE: 93
ctggaggact agaatcaatt agacatggac ttgggggcca tcacaccaca gagcccctca    60
cccacaggag tccgtgggtg agacctcctt cccttcctca caggacatgg ttatacttgg   120
c                                                                    121

<210> SEQ ID NO 94
<211> LENGTH: 121
<212> TYPE: DNA
<213> ORGANISM: Bos taurus

<400> SEQUENCE: 94
ggcataataa atataatgca cttgaatcat cctaaaacca tcctccctgc ctccccactc    60
ccaccagtcc atggaaatat tgtcttccat gaaaccggtc cctgcagcca aaaagtttgg   120
a                                                                    121

<210> SEQ ID NO 95
<211> LENGTH: 121
<212> TYPE: DNA
<213> ORGANISM: Bos taurus

<400> SEQUENCE: 95
attatttggt caatttggat ttcgcagaca attaaactgg ttaattcaga tcaaaatttc    60
ctcttcagat tctgacttat caggattggc acctacatta atttaattag tggaccaatg   120
g                                                                    121

<210> SEQ ID NO 96
<211> LENGTH: 121
<212> TYPE: DNA
<213> ORGANISM: Bos taurus

<400> SEQUENCE: 96
gtatttattt agacctcttt agaattgttc atgttttcaa ctcatacttt cgtaagtgga    60
cggcctgcta aggaaagcgc ctgacagtgc tgttgatgct tctgtaaagt ttggagcagt   120
a                                                                    121

<210> SEQ ID NO 97
<211> LENGTH: 121
<212> TYPE: DNA
```

<213> ORGANISM: Bos taurus

<400> SEQUENCE: 97

| attgcagaga gtaagaactg aaacaaggat gcccaagtgt gaaatctgca aaacaggtgc | 60 |
| gctgggtgtc ctgagctgtt ttctaatcct cacccccttg ctctgtgagc tgtcttctgt | 120 |
| g | 121 |

<210> SEQ ID NO 98
<211> LENGTH: 121
<212> TYPE: DNA
<213> ORGANISM: Bos taurus

<400> SEQUENCE: 98

| ccacaacata tctgaattta gaacacctca tcatgggcca aaatatcctg tttgtaatca | 60 |
| cgcttgccca cgacagaaac atatacaatc atccctgtca tctgcagggc attggttcca | 120 |
| g | 121 |

<210> SEQ ID NO 99
<211> LENGTH: 121
<212> TYPE: DNA
<213> ORGANISM: Bos taurus

<400> SEQUENCE: 99

| actgtccccg gaagggaagg gtgtcaagtg aatacaggca tggaggtgcc gatgaaaaga | 60 |
| gcctgggcct tgttcactca gctgtcgttc tcagtcagag tccgctccca ggaagactgc | 120 |
| t | 121 |

<210> SEQ ID NO 100
<211> LENGTH: 121
<212> TYPE: DNA
<213> ORGANISM: Bos taurus

<400> SEQUENCE: 100

| ataaggaaac aagtgtctta ccccacaaag caccagccct ccacagggtc cctcttatgg | 60 |
| gagaaagaca gctcagaact catgatcctt gaagtagggc aggagctagt taacacacac | 120 |
| a | 121 |

<210> SEQ ID NO 101
<211> LENGTH: 121
<212> TYPE: DNA
<213> ORGANISM: Bos taurus

<400> SEQUENCE: 101

| tgccatcatc tccattacat acaagaggaa cctaggtctt gagcagatta agtcaacttt | 60 |
| cccaggccat caatcatgag caaaagtctg tgatgtttcc ctggagacca cttcattccc | 120 |
| a | 121 |

<210> SEQ ID NO 102
<211> LENGTH: 121
<212> TYPE: DNA
<213> ORGANISM: Bos taurus

<400> SEQUENCE: 102

| cactgactga gttccaatga cttcagaaag aagagagaaa ggcatagctt gcatttacag | 60 |
| gagtatcatg tccatgtgaa ttttagcgtg caaagaattt tatgctatgg ttgaaatcag | 120 |
| a | 121 |

<210> SEQ ID NO 103
<211> LENGTH: 121
<212> TYPE: DNA
<213> ORGANISM: Bos taurus

<400> SEQUENCE: 103
gaagaactat ggtgtaatct ttccaatagc cttgtaaaca gagaacaaat cctcacaaaa      60
ggtatctttt acttgtggga caaagtaaac ttctggcaga tgtcaaatgt ttatactcgt     120
c                                                                    121

<210> SEQ ID NO 104
<211> LENGTH: 121
<212> TYPE: DNA
<213> ORGANISM: Bos taurus

<400> SEQUENCE: 104
ggaagccctt gcctaagtct aggcaggatc ttaagaatcc atggtggagg aatcttcata      60
tgctaaacaa aagtagtatt tcacatataa tagtttgcat gtgcaggtac tggtgatgac     120
c                                                                    121

<210> SEQ ID NO 105
<211> LENGTH: 121
<212> TYPE: DNA
<213> ORGANISM: Bos taurus

<400> SEQUENCE: 105
aaatcatatt tatctttgta tcaatcaatt cagtttaagt ttatatacat ttaatctgga      60
ccacctttgt aattacctgt ttactgtttg ttttcagaca gactgtaaat tcaaagaggc     120
a                                                                    121

<210> SEQ ID NO 106
<211> LENGTH: 121
<212> TYPE: DNA
<213> ORGANISM: Bos taurus

<400> SEQUENCE: 106
gaaccatcct tgtactgaag ccctctatac cagttagcct aacctgaatc accatgacag      60
gcaagtttct gccactgatt aattattttt aataagttct gtctcagaca aggtggtact     120
a                                                                    121

<210> SEQ ID NO 107
<211> LENGTH: 121
<212> TYPE: DNA
<213> ORGANISM: Bos taurus

<400> SEQUENCE: 107
agcaattcat caaatactca ctgactacct gcattcttcc ttttagtaat gtaacagata      60
cttattgatt ccctactaca tgcaaaaaac ttggtacagc attgagaaaa gtaattatga     120
a                                                                    121

<210> SEQ ID NO 108
<211> LENGTH: 121
<212> TYPE: DNA
<213> ORGANISM: Bos taurus

<400> SEQUENCE: 108

```
ggcagatcaa gggttcctct gtgataccat ctttcatgga cgcctttagg ggattgaact      60
ccttgtgtat gaatggccat tctgggggcc ttcctgtgag tctctggatc agcagagagc     120
c                                                                    121

<210> SEQ ID NO 109
<211> LENGTH: 121
<212> TYPE: DNA
<213> ORGANISM: Bos taurus

<400> SEQUENCE: 109
caccaacgac acagcctcag caggaacttc tctcttaatt agccttgagt aagaatttct      60
caacagagtg ctggaaccac tttgtcccaa atagcattat gattttcttc taatcagttc     120
a                                                                    121

<210> SEQ ID NO 110
<211> LENGTH: 121
<212> TYPE: DNA
<213> ORGANISM: Bos taurus

<400> SEQUENCE: 110
acctggatca agtccggtct gcggcctctc tgagtctggg cttcttgatt atgtggactg      60
gtatattccy ttttagacgt aagccagttt gagtcgcatt tgttaccact gcaacctga     120 t                                                                    121

<210> SEQ ID NO 111
<211> LENGTH: 121
<212> TYPE: DNA
<213> ORGANISM: Bos taurus

<400> SEQUENCE: 111
gccaagtaag tccctacaac tcctctttca tcccaagttg aaaacttagg tttcaaccct      60
caacccacct ctattcactt cctttctcac attctcaggg ggaagcttag agaacccatg     120
a                                                                    121

<210> SEQ ID NO 112
<211> LENGTH: 121
<212> TYPE: DNA
<213> ORGANISM: Bos taurus

<400> SEQUENCE: 112
ctttaggata acaaaagggt ctgatattca aatgagagtg attttcaaat gaatttcaaa      60
gggaagtgag gtggagtggt agggattccc accctcacac cacctgcccc cacagccctt     120
a                                                                    121

<210> SEQ ID NO 113
<211> LENGTH: 121
<212> TYPE: DNA
<213> ORGANISM: Bos taurus

<400> SEQUENCE: 113
atgtcactta tggttcccca gatactgctg tttaatcgct ttcaattacc tcaccccatg      60
cctacccaag ccaaatgaag tggtgagtca agcgattgtc tcgtgaatgg gatcaataca     120
g                                                                    121

<210> SEQ ID NO 114
<211> LENGTH: 121
```

```
<212> TYPE: DNA
<213> ORGANISM: Bos taurus

<400> SEQUENCE: 114
ccagccattt ctgagctcag aaaactatga aactcaccat tctttggcca ttctttgccg    60
cgccttattc ctttgaggaa acagtggaaa tttaaatgta tttgaagttc ttttctgca   120 g                                                                  121

<210> SEQ ID NO 115
<211> LENGTH: 121
<212> TYPE: DNA
<213> ORGANISM: Bos taurus

<400> SEQUENCE: 115
accctgagtg tgcactgcca gtgctgggct gtctgccaag cgcttagtat gaatgatcac    60
gcggccctga agccacactg tgcatagcag aaattctgtt cttgtctctg cctcaaagat   120
g                                                                  121

<210> SEQ ID NO 116
<211> LENGTH: 121
<212> TYPE: DNA
<213> ORGANISM: Bos taurus

<400> SEQUENCE: 116
cgtccatggg gtcccaaaaa gtcagacatg actgagtgac tgaattgact gactgactga    60
caaggataat ctttagtttg tcataactat tgcaactatt ttgttcttat ttgacattaa   120
c                                                                  121

<210> SEQ ID NO 117
<211> LENGTH: 121
<212> TYPE: DNA
<213> ORGANISM: Bos taurus

<400> SEQUENCE: 117
gggagtcctg aaacaggagc tccctgtac agggaaattc cttcgcagcc gggcctaagg     60
gggagctgca gagtcttgaa aaaccaggca agcagggac ttagagggca ggaaacagag    120
a                                                                  121

<210> SEQ ID NO 118
<211> LENGTH: 121
<212> TYPE: DNA
<213> ORGANISM: Bos taurus

<400> SEQUENCE: 118
gagggaagga tctgttccag gcctctctcc tcagcctact gatggccagc ttccctctcc    60
gcatacctgt atccaaattt ccccttttta taaggacacc agttatattg gatagggcc   120 c                                                                  121

<210> SEQ ID NO 119
<211> LENGTH: 121
<212> TYPE: DNA
<213> ORGANISM: Bos taurus

<400> SEQUENCE: 119
gtattttttc ctcctttgct tatatttaga gagtaattta aaaatagatt acagaaagat    60
ggaacactct agagtggctg ctttcctag ctgagctctt aaaagcactc cagattgtta   120
```

| | |
|---|---|
| a | 121 |

<210> SEQ ID NO 120
<211> LENGTH: 121
<212> TYPE: DNA
<213> ORGANISM: Bos taurus

<400> SEQUENCE: 120

| | |
|---|---|
| actcctcctg aaaatagaga aaccctctgt ctgacttcca gggcaaaccg catggaagca | 60 |
| cacaccagaa aagattctgt ggcagaaaat agaaatggct gctggataat actggagctg | 120 |
| a | 121 |

<210> SEQ ID NO 121
<211> LENGTH: 121
<212> TYPE: DNA
<213> ORGANISM: Bos taurus

<400> SEQUENCE: 121

| | |
|---|---|
| actggtgact ttcaatcaca gtgaagactg agtcccagcc attttatgac agtggtcacg | 60 |
| cgattcttac cccatcatct gcctctaggc tgggccatgg caacagggcc ggtgaggggt | 120 |
| g | 121 |

<210> SEQ ID NO 122
<211> LENGTH: 121
<212> TYPE: DNA
<213> ORGANISM: Bos taurus

<400> SEQUENCE: 122

| | |
|---|---|
| cctatacata acctggctct gtggtcagca gggcttgtag gcatggggcc tacaagatca | 60 |
| cgaccagtag ataaagagtt tttaaacagc tccctagccc ttatgtacca gaggcgatag | 120 |
| a | 121 |

<210> SEQ ID NO 123
<211> LENGTH: 121
<212> TYPE: DNA
<213> ORGANISM: Bos taurus

<400> SEQUENCE: 123

| | |
|---|---|
| gagaattcca aagtgacacc cacaggcact gggatcagca aagtggcctg aaattgcaaa | 60 |
| gatggctccc tccggtttct cagttcccag ggagcatcca aaatgggtcc agcagatgct | 120 |
| c | 121 |

<210> SEQ ID NO 124
<211> LENGTH: 121
<212> TYPE: DNA
<213> ORGANISM: Bos taurus

<400> SEQUENCE: 124

| | |
|---|---|
| acagtcacca agagaagaca gaagtcagat tgcatagcag ccagaaggaa tcaaaaacag | 60 |
| gctcagctga cccaaaggct acaaggccac aaatgtcaag ttcttccctc agtgcctgct | 120 |
| g | 121 |

<210> SEQ ID NO 125
<211> LENGTH: 121
<212> TYPE: DNA
<213> ORGANISM: Bos taurus

<400> SEQUENCE: 125

```
ccattcctcc ctgctggcaa ccacaagtct attttttgtt tctgggccca catgtacttc     60
gaattgttaa atgcaattca attccatttg gtttatgaac gtgtcactcc ttcccatgaa    120
c                                                                   121

<210> SEQ ID NO 126
<211> LENGTH: 121
<212> TYPE: DNA
<213> ORGANISM: Bos taurus

<400> SEQUENCE: 126
gaggctggaa tcaaaggagg catttccagg catatcttta tttttacatt accagaaatc     60
ccatatgggg ttgactagtt agtttagatg ctcagggctt tggtttcagg gctaatgaca    120
a                                                                   121

<210> SEQ ID NO 127
<211> LENGTH: 121
<212> TYPE: DNA
<213> ORGANISM: Bos taurus

<400> SEQUENCE: 127
acctttccat caagcaatca tttcctctct ttcctgtaag tcttagaatg gttaatagcc     60
gagtcttccc tttcttttga ccaattctca cctctggttt gttcctcatt gttgtgacat    120
a                                                                   121

<210> SEQ ID NO 128
<211> LENGTH: 121
<212> TYPE: DNA
<213> ORGANISM: Bos taurus

<400> SEQUENCE: 128
gtgctgcgaa cagacccta aaggaaaagg cttctccagg gaactgggaa gaaagggaag      60
cagaacagaa ggccctgcca gaccttctaa ccttcctctg aggcttcttt tttaatcatc    120
a                                                                   121

<210> SEQ ID NO 129
<211> LENGTH: 121
<212> TYPE: DNA
<213> ORGANISM: Bos taurus

<400> SEQUENCE: 129
aattccatga atggaggagc ctcgtgggct acagtccatg ggatcgcaaa gaaacacaac     60
ctcgaggcta acaacaaca acaagggtac cgttctaagt acatacatat caagttcctg    120
a                                                                   121

<210> SEQ ID NO 130
<211> LENGTH: 121
<212> TYPE: DNA
<213> ORGANISM: Bos taurus

<400> SEQUENCE: 130
agaaaagaga atctctcctt taagaaaagg atttacgtaa attactgtca aatgttctac     60
ccctgagcta tatacccttt gtttcaattg aaaccacttt tttttttttc cagtgaaata    120
a                                                                   121

<210> SEQ ID NO 131
```

```
<211> LENGTH: 121
<212> TYPE: DNA
<213> ORGANISM: Bos taurus

<400> SEQUENCE: 131
cagtatgaag gaaagttacc aaaactgact tgtaggaact tcctagcagt tcagtgggta    60
cggctcagtg ctcccaacgc aggggggcctg ggttcaatcc ttggccaggg aactgagtct   120
c                                                                    121

<210> SEQ ID NO 132
<211> LENGTH: 121
<212> TYPE: DNA
<213> ORGANISM: Bos taurus

<400> SEQUENCE: 132
agaattggcg tggagctgtc atgtcaatag acagtcttcc cacagaggga caacccaacc    60
gtccctaaaa gttctcacag gacatttggc agcatctcca gtaactcagc caatattact   120
c                                                                    121

<210> SEQ ID NO 133
<211> LENGTH: 121
<212> TYPE: DNA
<213> ORGANISM: Bos taurus

<400> SEQUENCE: 133
atactttgtc tctgtttgtc gccccagcct aaaaagatcc aatccagggt ggcaagatat    60
ctccatattt gctactgact taagaactga ctcatttgaa aagaccccga tgctgggaaa   120
g                                                                    121

<210> SEQ ID NO 134
<211> LENGTH: 121
<212> TYPE: DNA
<213> ORGANISM: Bos taurus

<400> SEQUENCE: 134
ctgagggtcc agtctcagcg atggggcttg ccgggctgcg ctcttccgca gtaggctctg    60
gggggacggg ggcaggcacc aggagaaagg ataaaggtca cagtgagact atgctgggtc   120
a                                                                    121

<210> SEQ ID NO 135
<211> LENGTH: 121
<212> TYPE: DNA
<213> ORGANISM: Bos taurus

<400> SEQUENCE: 135
atgtttctgt atgatggaag tgaggcaagg tggaagactg gctcccagtt tgacctgctg    60
gaaccacagg ggccgtggcc tattgcaatg acagcctaca atcaagtatc tcttgactgt   120
a                                                                    121

<210> SEQ ID NO 136
<211> LENGTH: 121
<212> TYPE: DNA
<213> ORGANISM: Bos taurus

<400> SEQUENCE: 136
acaaaataat catagttact aatatttgaa tctattcaca aaaatagagc aagccctcaa    60
caatagcacg atctaaatga caaacttttc aacaaaacta ggtaggatgg tatcctcaca   120
``` a                                                                            121

<210> SEQ ID NO 137
<211> LENGTH: 121
<212> TYPE: DNA
<213> ORGANISM: Bos taurus

<400> SEQUENCE: 137
ggagggacca aaacaagac agacaaacag attccttttt aaggctgagt aaacgaagat      60
cgtggcatct ggccctgtca cttcatggga aatagatggg gaaacagtgg aaacagtgtc    120
a                                                                            121

<210> SEQ ID NO 138
<211> LENGTH: 121
<212> TYPE: DNA
<213> ORGANISM: Bos taurus

<400> SEQUENCE: 138
agcagtcgct catggagtca gaattcagat gggaactggg gctgtggcag aaatctgccc     60
ggtggaaact gtggccacag aacggacttc tagaaagaga tggaattacg gagactccga   120
t                                                                            121

<210> SEQ ID NO 139
<211> LENGTH: 121
<212> TYPE: DNA
<213> ORGANISM: Bos taurus

<400> SEQUENCE: 139
atgaacaact atagccagga gcaatggaga aatcaccttg ctagcaggcc caagggaatt     60
gccaccgagt gcctgcactg ctgtgggctg gcaggaccca gagatgcact gtcaggcggg   120
g                                                                            121

<210> SEQ ID NO 140
<211> LENGTH: 121
<212> TYPE: DNA
<213> ORGANISM: Bos taurus

<400> SEQUENCE: 140
atcttgactg aagtggtgat tacaggtgta tacgtttgtc aaaatttgaa aagggtgcat     60
cctgtatttt attgtgaata aactataccta caataaaaact gaattaaaaa gaaaatccaa  120
a                                                                            121

<210> SEQ ID NO 141
<211> LENGTH: 121
<212> TYPE: DNA
<213> ORGANISM: Bos taurus

<400> SEQUENCE: 141
acacatatag cataagaaga tgggaccaaa atgtcttcac ttttacactc aaggacttgt     60 gtttttttt gcggatgggt ggcaggggag aagggtgtcc acaactgctt aaggaccaag    120
a                                                                            121

<210> SEQ ID NO 142
<211> LENGTH: 121
<212> TYPE: DNA
<213> ORGANISM: Bos taurus

<400> SEQUENCE: 142
ggttatgaag ctctactata cttacgcaag accacgactt ttcagggaaa ctgggaaaag    60
ggcatactag ctctttctga attatttctt acaactgcat gagaatctac aacaatatcc   120
a                                                                  121

<210> SEQ ID NO 143
<211> LENGTH: 121
<212> TYPE: DNA
<213> ORGANISM: Bos taurus

<400> SEQUENCE: 143
agccctggtc agcaccatgt gaagcagaag aaatgcctgg gcaatgcaca gaaccacgag    60
tgagagtaca tgttgttact gtaagtctct agggcttagg agatttgtta cccagcaata   120
g                                                                  121

<210> SEQ ID NO 144
<211> LENGTH: 121
<212> TYPE: DNA
<213> ORGANISM: Bos taurus

<400> SEQUENCE: 144
acatggaaat agctttgttt cataacactc tctttgtatt ttttggttgt tgttataatg    60
gaattttgtt gtatatggcc ctgaattcta ctaagtgctt cagacttgaa gagtttggtt   120
g                                                                  121

<210> SEQ ID NO 145
<211> LENGTH: 121
<212> TYPE: DNA
<213> ORGANISM: Bos taurus

<400> SEQUENCE: 145
caggtccttt gaatttcctt tgggctcagc cagtgggagg ccacagtggg agtgaagaga    60
gaagggctgg gtcacctttc tgtcctgtgt cccctctct gtggggtctg cttaggctgc    120
c                                                                  121

<210> SEQ ID NO 146
<211> LENGTH: 121
<212> TYPE: DNA
<213> ORGANISM: Bos taurus

<400> SEQUENCE: 146
agtcagacac aactgtgcaa ccaacacaac acacactgac taaccctcc ttgccacttc    60 cactgcctgc tctctggcca tccctacttt ttatctggat ctcctaactt gccttccatc   120
c                                                                  121

<210> SEQ ID NO 147
<211> LENGTH: 121
<212> TYPE: DNA
<213> ORGANISM: Bos taurus

<400> SEQUENCE: 147
ctgaaacaaa tactgggata tcagacaggt ctctagagaa cccacccaca aaaaagatt    60 ctaatataag acaaactacc tgtagttttc tgttttcctt tttcttttt tgatattgac   120 a                                                                  121

<210> SEQ ID NO 148
<211> LENGTH: 121
<212> TYPE: DNA
<213> ORGANISM: Bos taurus

<400> SEQUENCE: 148
caagaagcac ccgggctcca ggggaaggca tgtgggcagg cttccacctg tcccttgggg    60
cgctaaggcc agaagggaag aggggtagg atggagagca accccagctg tgaacacaac   120
c                                                                   121

<210> SEQ ID NO 149
<211> LENGTH: 121
<212> TYPE: DNA
<213> ORGANISM: Bos taurus

<400> SEQUENCE: 149
actggatgag tgtataatta tgtgcatcca caattatatt ttcataaaga gtaatttcac    60
cgtcctgaga gtcccctctt cctctctcac tactagtccc tggtaaccac tgatatcttg   120
a                                                                   121

<210> SEQ ID NO 150
<211> LENGTH: 121
<212> TYPE: DNA
<213> ORGANISM: Bos taurus

<400> SEQUENCE: 150
aactaaagac ttgagaagag taaattgata gagcataata gtgtttggca caaggaaagg    60
catgtgtaga tgagagcgtg ctgggaaaag gtgcttacat ataacacaag caaaattaca   120
c                                                                   121

<210> SEQ ID NO 151
<211> LENGTH: 121
<212> TYPE: DNA
<213> ORGANISM: Bos taurus

<400> SEQUENCE: 151
tgcaccaaaa ttccttttct aaaacttagt aagacttggc accaattgcc aacattgcta    60
gttgtctttc tgatttttt ttttttttt gcatctctta gtcttacaaa ctactgcaca   120
a                                                                   121

<210> SEQ ID NO 152
<211> LENGTH: 121
<212> TYPE: DNA
<213> ORGANISM: Bos taurus

<400> SEQUENCE: 152
agaaaaaaaa aaaagaccag caaggtaagg gaaagagagt ggccactgac cacctccccc    60
ggatcaatcc ccttctagct ctctccccga gagggcttat ctcttgtagg gagaggtctc   120
t                                                                   121

<210> SEQ ID NO 153
<211> LENGTH: 121
<212> TYPE: DNA
<213> ORGANISM: Bos taurus

<400> SEQUENCE: 153
accatccttc ttcccctcta gaatatgcta tctgtaattt tatttccagt gcttggtacc    60

```
gtaattggaa tataaactgt ttatcaaata catgttgaat caaggctaag cacagagcaa    120
a                                                                    121

<210> SEQ ID NO 154
<211> LENGTH: 121
<212> TYPE: DNA
<213> ORGANISM: Bos taurus

<400> SEQUENCE: 154
acaggaattt tgacccatag cttgtggtcc accagagcag ccacagggcc tccgccagca    60
cgctaaatgt tctatccctg cttctgccaa ggaatgttga tcagatcatg tagccctgtc    120
c                                                                    121

<210> SEQ ID NO 155
<211> LENGTH: 121
<212> TYPE: DNA
<213> ORGANISM: Bos taurus

<400> SEQUENCE: 155
cctagcctca tgcttcgttc aaaaaccaat agccatttta ttggtttctc aagaaagaaa    60
gaaagtaaaa gcaatcatag gccatcacca taggccatct gatggcctgt atgctagcac    120
a                                                                    121

<210> SEQ ID NO 156
<211> LENGTH: 121
<212> TYPE: DNA
<213> ORGANISM: Bos taurus

<400> SEQUENCE: 156
cagctttctt caccgtccaa ctctcacatc catacatgac tactggacaa ttggactatc    60
cgtatttaag cttgtctcct ttttgaggta gtcatttctt aagttggcaa gtgtctttat    120
g                                                                    121

<210> SEQ ID NO 157
<211> LENGTH: 121
<212> TYPE: DNA
<213> ORGANISM: Bos taurus

<400> SEQUENCE: 157
aacagggctc tatgtccaag gaaaccagcc agtcacccgg tggcaggatg atcataggtg    60
gttcttttca atatggagag gccagagact agtcctcaga aaaataaacc tcttggatat    120
g                                                                    121

<210> SEQ ID NO 158
<211> LENGTH: 121
<212> TYPE: DNA
<213> ORGANISM: Bos taurus

<400> SEQUENCE: 158
aaaggagagt acaccctcaa ggcatgaggg tgagtggacc ccaaaggaga ggccttaatc    60
catcttgacc ttctcctttt atatgtttgt cttctcccca ccttgagcct gccttctgca    120
a                                                                    121

<210> SEQ ID NO 159
<211> LENGTH: 121
<212> TYPE: DNA
<213> ORGANISM: Bos taurus
```

<400> SEQUENCE: 159
taaacatgac taggtcattt gaatgtctct ttgagaaaat ttaccatggc acttactcta    60
gtcattgggc ttcccccatg gcactagtgg taagaaccca ccgaccaatg caggagatgc   120
a                                                                  121

<210> SEQ ID NO 160
<211> LENGTH: 121
<212> TYPE: DNA
<213> ORGANISM: Bos taurus

<400> SEQUENCE: 160
tgagcatgag tgttgcagag cagcagaaag aagtagaata cttcttagct tccgtggtgg    60
ctacttatgt caatagttgt gtggagcgct tgccccacgg tggccctctg atgccaaaac   120
a                                                                  121

<210> SEQ ID NO 161
<211> LENGTH: 121
<212> TYPE: DNA
<213> ORGANISM: Bos taurus

<400> SEQUENCE: 161
agtttgctgt tatttgtgaa ggatactttt gctaaatata gaaatcttgg ttgacagttt    60
cgttctctga gtaccgaatg catcactcca ctgtctttga cctctgttgc ttctgatgag   120
a                                                                  121

<210> SEQ ID NO 162
<211> LENGTH: 121
<212> TYPE: DNA
<213> ORGANISM: Bos taurus

<400> SEQUENCE: 162
agtactgcgg aaatggattg cagtcacaac tggctttgaa gaggccaatt acaaggtaaa    60
ttttccatat atcctttaag gtaaagaaaa aagaataaa atccccaaa tggccagaga    120 a                                                                  121

<210> SEQ ID NO 163
<211> LENGTH: 121
<212> TYPE: DNA
<213> ORGANISM: Bos taurus

<400> SEQUENCE: 163
agagggttat aaacacatca taaaatctga cctttccaag aggggattat ctataaataa    60
ctgtggtgct aggcataagc ctggtggagg ggctgagagg agggtaattt cctctactcc   120
c                                                                  121

<210> SEQ ID NO 164
<211> LENGTH: 121
<212> TYPE: DNA
<213> ORGANISM: Bos taurus

<400> SEQUENCE: 164
catccatctt gtagccctga aaacaacagc aagaagataa acagagcact gagagggaca    60
cggccgtcca ctcagaccca gaacacagac aactcccagg aaactgcagt ggacagaagc   120
c                                                                  121

<210> SEQ ID NO 165
<211> LENGTH: 121
<212> TYPE: DNA
<213> ORGANISM: Bos taurus

<400> SEQUENCE: 165
aatcaggccc cagacagggg gaaaaaaaaa tgctaagcaa gactgctata gggggtcctg    60
gaactaggga agcttcttca gggccttttc tctgtgggtg ataatctttt cacttcccca   120
c                                                                   121

<210> SEQ ID NO 166
<211> LENGTH: 121
<212> TYPE: DNA
<213> ORGANISM: Bos taurus

<400> SEQUENCE: 166
atatgttctg tcttttcat tatatttgtc aatgtcttgg ttctcccttt attatctctt    60
gcctggactc ttcaagtagt cttacaaatg tcttcagctt ctctccaacc ccttcaatta   120
g                                                                   121

<210> SEQ ID NO 167
<211> LENGTH: 121
<212> TYPE: DNA
<213> ORGANISM: Bos taurus

<400> SEQUENCE: 167 cttttcacc agctgccttg gctgtgtgaa cttctctctc gataatcatc ccttatccca    60
catcccagtg tggccctgct tcccctatca agccctaact gatacactag gtaaatgaga   120
c                                                                   121

<210> SEQ ID NO 168
<211> LENGTH: 121
<212> TYPE: DNA
<213> ORGANISM: Bos taurus

<400> SEQUENCE: 168
ccttccctcc ctggagggga gggttctcca cagcttccac ggtggccaga gggctccccc    60
cacaaccaca cctgtgaaca gtctcctctg ctccaccttn gggcagggag gagccccatc   120
c                                                                   121

<210> SEQ ID NO 169
<211> LENGTH: 121
<212> TYPE: DNA
<213> ORGANISM: Bos taurus

<400> SEQUENCE: 169
cgccaggctc ggaatgggac ctcacccaca ccttcttctc gcccaggtgt ctgttcttac    60
gttcagggca gcccccctgg tggccccag ggttgggact taaagccact gtccgcaagt   120
c                                                                   121

<210> SEQ ID NO 170
<211> LENGTH: 121
<212> TYPE: DNA
<213> ORGANISM: Bos taurus

<400> SEQUENCE: 170
gcaatgcagc ttggttagtt cccttaggct ccaccagcgc tgtgttatgg agcacgtgac    60

```
cggtcgtggg ccatcaccat ctgacatacg acagtcatga gctactagaa acattcagtc    120
c                                                                    121

<210> SEQ ID NO 171
<211> LENGTH: 121
<212> TYPE: DNA
<213> ORGANISM: Bos taurus

<400> SEQUENCE: 171
aatttagcaa agaagcctag cttttataaa agatcaaaca tttcacttta taaaaacact    60
cccagtgatg gtcacttgac tttcctcaag acttttagct gtggtgataa aacaacagga    120
c                                                                    121

<210> SEQ ID NO 172
<211> LENGTH: 121
<212> TYPE: DNA
<213> ORGANISM: Bos taurus

<400> SEQUENCE: 172
aaagtattat aaacctatta catttttct tgcttttac caagcaaatt gacaacattt       60
gaaaaaggat cattgaaaga atatgaggaa tcacatattg gtgggaatgc aaagtgtaag    120
t                                                                    121

<210> SEQ ID NO 173
<211> LENGTH: 121
<212> TYPE: DNA
<213> ORGANISM: Bos taurus

<400> SEQUENCE: 173
agacacgtat ttgcatcatg catttgtgtg tcccttcct aaagagacgt ctcttgtaga     60
cgtcactgtg tggcctgtat tcctagcctc agccgaggcc tcctcattga acaccagtca    120
c                                                                    121

<210> SEQ ID NO 174
<211> LENGTH: 121
<212> TYPE: DNA
<213> ORGANISM: Bos taurus

<400> SEQUENCE: 174
cccagacaca caatcacacg taattgaatt ggagtcctgg taaacatgtg tggcttcttt    60
ctttaatagc tgggtgaatt gccattccaa ataaaattgg gattattata aatgaagaag    120
g                                                                    121

<210> SEQ ID NO 175
<211> LENGTH: 121
<212> TYPE: DNA
<213> ORGANISM: Bos taurus

<400> SEQUENCE: 175
tagtatggcc agaacttgat cattacaggg aaagcgtgaa ggtggaattt ggagaagaag    60
gtatagaaca gcttctgcat ggcccattaa agaagtatgg gttttatgta aagagtattg    120
a                                                                    121

<210> SEQ ID NO 176
<211> LENGTH: 121
<212> TYPE: DNA
```

<213> ORGANISM: Bos taurus

<400> SEQUENCE: 176

| acaggacagc tgaaaaagag caatacaagt cccgtgtttt aaaagtagaa gataagacat | 60 |
| gctggagcag gtagagagaa aggacttctc ctacactgtt ggtgggaata taagttgggg | 120 |
| c | 121 |

<210> SEQ ID NO 177
<211> LENGTH: 121
<212> TYPE: DNA
<213> ORGANISM: Bos taurus

<400> SEQUENCE: 177

| cccggcatca gtaatgacac ttgttattaa caattaggtt gcattatgtt gcttcagaac | 60 |
| gcggctcctt gtcagcagca ctggcctgcc agttgctcgc ttacagcctg gccctcagaa | 120 |
| g | 121 |

<210> SEQ ID NO 178
<211> LENGTH: 121
<212> TYPE: DNA
<213> ORGANISM: Bos taurus

<400> SEQUENCE: 178

| ggggcatgtt ccagacaatg ctaaatgcag atatgaacct cttcagggtg ctgaatcccc | 60 |
| cctgtgctga gatccccagc tccgactaag cctctgccct ccaagatggt cagatttctg | 120 |
| a | 121 |

<210> SEQ ID NO 179
<211> LENGTH: 121
<212> TYPE: DNA
<213> ORGANISM: Bos taurus

<400> SEQUENCE: 179

| caccagagct aatgagccct tttcctatca tgaagcctgg aaaggagttg gagaggcaaa | 60 |
| ctcgaatcag aaacatctct ctggggactt ttttcttttt gcaaagggac cagaaagaaa | 120 |
| g | 121 |

<210> SEQ ID NO 180
<211> LENGTH: 121
<212> TYPE: DNA
<213> ORGANISM: Bos taurus

<400> SEQUENCE: 180

| acactcctat ggtgcactcc ccactccctg cgcatgatga aaggactttg caaacactca | 60 |
| gtgggcacag caggcccaag aggtgaggga agttgtcgac cccatcttac ggataaggaa | 120 |
| a | 121 |

<210> SEQ ID NO 181
<211> LENGTH: 121
<212> TYPE: DNA
<213> ORGANISM: Bos taurus

<400> SEQUENCE: 181

| gcatataatc catcaaatga gggtaactgt tctattttgt atttttaata cctgagtgtt | 60 |
| ggtcatacaa tctcttccta agggaagcta taacttagta gagctctaat tacaatgcaa | 120 |
| a | 121 |

<210> SEQ ID NO 182
<211> LENGTH: 121
<212> TYPE: DNA
<213> ORGANISM: Bos taurus

<400> SEQUENCE: 182

```
ggattctttta ccactgagcc accttgggaa accccattc actttgtac ttaaggccaa      60
gatgtatctt ttctcataaa tatgtcctct gttagtaaat cttatgagaa tgttttaagc    120
c                                                                    121
```

<210> SEQ ID NO 183
<211> LENGTH: 121
<212> TYPE: DNA
<213> ORGANISM: Bos taurus

<400> SEQUENCE: 183

```
aagacacact tgtaggagcc tgctggaaca ctccagggac aaggcccggt gggtgacacc     60
gtcatactct cccttttgccg tgctccggag gtccagaatc tcccaggaga aagcttatac  120
t                                                                    121
```

<210> SEQ ID NO 184
<211> LENGTH: 121
<212> TYPE: DNA
<213> ORGANISM: Bos taurus

<400> SEQUENCE: 184

```
tccctcccac catcaacctg gcttgctctc ctgcttccct aatgcaagtt gaaagaagaa     60
cctatgtgcc tgctgccatc cactattcaa ccaaaactgg atcccagcat caccaaataa   120
a                                                                    121
```

<210> SEQ ID NO 185
<211> LENGTH: 121
<212> TYPE: DNA
<213> ORGANISM: Bos taurus

<400> SEQUENCE: 185

```
caagttctag atgggtgaaa acctacgtct gtctttcctt ttgtagccag tcttccttat     60
gcatagcaga agctcacaaa cggtaattta ataggaataa aaggagtgta tctttgaacc   120
g                                                                    121
```

<210> SEQ ID NO 186
<211> LENGTH: 121
<212> TYPE: DNA
<213> ORGANISM: Bos taurus

<400> SEQUENCE: 186

```
caactttatt ttttttattc tacaaacaat ttattgctct gtgaaaagta ttcaatgaaa     60
gtttcaggcc caattgagtt gcgtcccttt ggccacgtgc ccttcatttt ggcaaagggc   120
c                                                                    121
```

<210> SEQ ID NO 187
<211> LENGTH: 121
<212> TYPE: DNA
<213> ORGANISM: Bos taurus

<400> SEQUENCE: 187

```
aactcctcat cttcatctaa cccagacaat ctacaatatt cattaccact cttggccagg    60
gattagggag taagtgctta gaaaatagtg gttctgaaaa attaccatct attggatatg   120
c                                                                  121
```

<210> SEQ ID NO 188
<211> LENGTH: 121
<212> TYPE: DNA
<213> ORGANISM: Bos taurus

<400> SEQUENCE: 188

```
ccacgaggaa gtgaaacctg tcaacaccaa ccacagggt gagcttggaa gtggatctgt    60
cggccctagt tgagccttga gatgacagca gaccaggctg cacctccac tctaacttca   120 a                                                                  121
```

<210> SEQ ID NO 189
<211> LENGTH: 121
<212> TYPE: DNA
<213> ORGANISM: Bos taurus

<400> SEQUENCE: 189

```
agcaacgaga cggaaggggc ctgggcccct ggtgctggcc ccgcccttg ggcagctaac    60 gggagaaaga gtcggctttc cactcttgaa gctgccagcc ggcatctctg gcgtcgcaaa   120
c                                                                  121
```

<210> SEQ ID NO 190
<211> LENGTH: 121
<212> TYPE: DNA
<213> ORGANISM: Bos taurus

<400> SEQUENCE: 190

```
tctctttctc tctggctaga agcaaatgac cccatgatgg cagagccaca ccatgaagag    60
cctgggcctc tgagtcagtg cttacaggat gaggggggcca ggaggtcctc ttgccggggc   120
a                                                                  121
```

<210> SEQ ID NO 191
<211> LENGTH: 121
<212> TYPE: DNA
<213> ORGANISM: Bos taurus

<400> SEQUENCE: 191

```
caagaacagg gtatagtttt gtgatagctt gaaggcaaga gagcacatgg cctattctgg    60
gaactatagg aatagaatgg ctctgtcata ggattgaagt ggtaaaagaa gacatgggag   120
a                                                                  121
```

<210> SEQ ID NO 192
<211> LENGTH: 121
<212> TYPE: DNA
<213> ORGANISM: Bos taurus

<400> SEQUENCE: 192

```
aacctcagga gtctatagat taaaatattt gcttgacctt taatacaagc aggaacccaa    60
caattccagc aataattaca aaaatattac tacctcccgt ttattaagca tttattttcc   120
t                                                                  121
```

<210> SEQ ID NO 193
<211> LENGTH: 121

```
<212> TYPE: DNA
<213> ORGANISM: Bos taurus

<400> SEQUENCE: 193
tgtcgcctct gtaaatggag gtaatcttag actccacctc aaagggctca tgtgacgatc      60
gcaggagaca atgcccataa aattctgggg acagtgcctg actcagagaa agcgctgcac     120
a                                                                     121

<210> SEQ ID NO 194
<211> LENGTH: 121
<212> TYPE: DNA
<213> ORGANISM: Bos taurus

<400> SEQUENCE: 194
ctcccaacca ggtttcttga gctataatca aaacaaatgg taggccaggt gggggatgag      60
gcatttactc ttagttaagc acagactgca ttttttaat ataggaaaat cttaaaatgg     120
c                                                                     121

<210> SEQ ID NO 195
<211> LENGTH: 121
<212> TYPE: DNA
<213> ORGANISM: Bos taurus

<400> SEQUENCE: 195
cctggctatg gatttgtata caggcaggag ttttgttcag gttgtctttt aatttctaga      60
gcttagcaca gataccctat tgatacaata acatttgag aagggaaga gaaataaagg     120 a                                                                     121

<210> SEQ ID NO 196
<211> LENGTH: 121
<212> TYPE: DNA
<213> ORGANISM: Bos taurus

<400> SEQUENCE: 196
actctcagca gaaacacat tgagcaggga gggtcttaga gacaggacaa gaactatccc      60
cggacaattt tactctccct gaaggcccct cctctttcac tctctacccc attcttcaca    120
t                                                                     121

<210> SEQ ID NO 197
<211> LENGTH: 121
<212> TYPE: DNA
<213> ORGANISM: Bos taurus

<400> SEQUENCE: 197
ccacagaagt ggaatcgtgt cgtatttgtc ctttcatacc tggcctcttt cagtttgtgt      60
gacggcttcc aggtttatcc acgctgtacc aggtgtcaga atttccttct tttttgagg     120 c                                                                     121
```